United States Patent
Badylak et al.

[11] Patent Number: 6,126,686
[45] Date of Patent: Oct. 3, 2000

[54] ARTIFICIAL VASCULAR VALVES

[75] Inventors: Stephen F. Badylak, West Lafayette, Ind.; Arthur C. Coffey, Annadale, Va.; Leslie A. Geddes, West Lafayette; Michael C. Hiles, Lafayette, both of Ind.; James Hong, Waterloo, Ill.; Rebecca Roeder, Lafayette, Ind.

[73] Assignee: Purdue Research Foundation, West Lafayette, Ind.

[21] Appl. No.: 09/319,653

[22] PCT Filed: Dec. 10, 1997

[86] PCT No.: PCT/US97/22728

§ 371 Date: Jun. 10, 1999

§ 102(e) Date: Jun. 10, 1999

[87] PCT Pub. No.: WO98/25549

PCT Pub. Date: Jun. 18, 1998

Related U.S. Application Data

[60] Provisional application No. 60/032,684, Dec. 10, 1996.

[51] Int. Cl.$^7$ .................................................. A61F 2/06
[52] U.S. Cl. .................. 623/1.24; 623/910; 623/918; 623/925; 623/1.26; 623/2.13
[58] Field of Search ................. 623/1.24, 1.26, 623/2.13, 2.15, 2.17, 2.19, 909, 918, 925

[56] References Cited

U.S. PATENT DOCUMENTS

| | | |
|---|---|---|
| 3,320,972 | 5/1967 | High et al. . |
| 3,445,916 | 5/1969 | Schulte . |
| 3,562,820 | 2/1971 | Braun . |
| 3,736,598 | 6/1973 | Bellhouse et al. . |
| 4,084,268 | 4/1978 | Ionescu et al. . |
| 4,247,292 | 1/1981 | Angell . |
| 4,470,157 | 9/1984 | Love . |
| 4,902,508 | 2/1990 | Badylak et al. . |
| 5,156,621 | 10/1992 | Navia et al. . |
| 5,275,826 | 1/1994 | Badylak et al. . |
| 5,281,422 | 1/1994 | Badylak et al. . |
| 5,480,424 | 1/1996 | Cox . |
| 5,554,389 | 9/1996 | Badylak et al. . |
| 5,713,950 | 2/1998 | Cox . |
| 5,824,063 | 10/1998 | Cox . |

FOREIGN PATENT DOCUMENTS

| | | |
|---|---|---|
| 133420 | 2/1985 | European Pat. Off. . |
| 155245 | 9/1985 | European Pat. Off. . |
| 275535 | 7/1988 | European Pat. Off. . |
| 276975 | 8/1988 | European Pat. Off. . |
| 515324 | 11/1992 | European Pat. Off. . |
| 2391708 | 12/1978 | France . |
| 355959 | 6/1975 | Germany . |
| 477643 | 6/1977 | United Kingdom . |
| 599407 | 9/1981 | United Kingdom . |
| 95/16411 | 6/1995 | WIPO . |
| 96/31226 | 10/1996 | WIPO . |
| 97/24082 | 7/1997 | WIPO . |

OTHER PUBLICATIONS

Love. *Autologous Tissue Heart Valves*. R. G. Landes Company, 1993, pp. 1–22.

*Primary Examiner*—David H. Willse
*Assistant Examiner*—Brian Pellegrino
*Attorney, Agent, or Firm*—Barnes & Thornburg

[57] ABSTRACT

A method for preparing vascular valves from submucosal tissue is described. Both bicuspid and tricuspid valve constructs are described. The bicuspid constructs can be formed with or without a supporting stent. The tricuspid constructs are formed by fixing submucosal tissue to a supporting stent, folding the submucosal tissue, and forming the valve commissures from the folded submucosal tissue by cutting along the folds. The artificial vascular valves are useful for replacing damaged or diseased valves of a warm-blooded vertebrate.

18 Claims, 7 Drawing Sheets

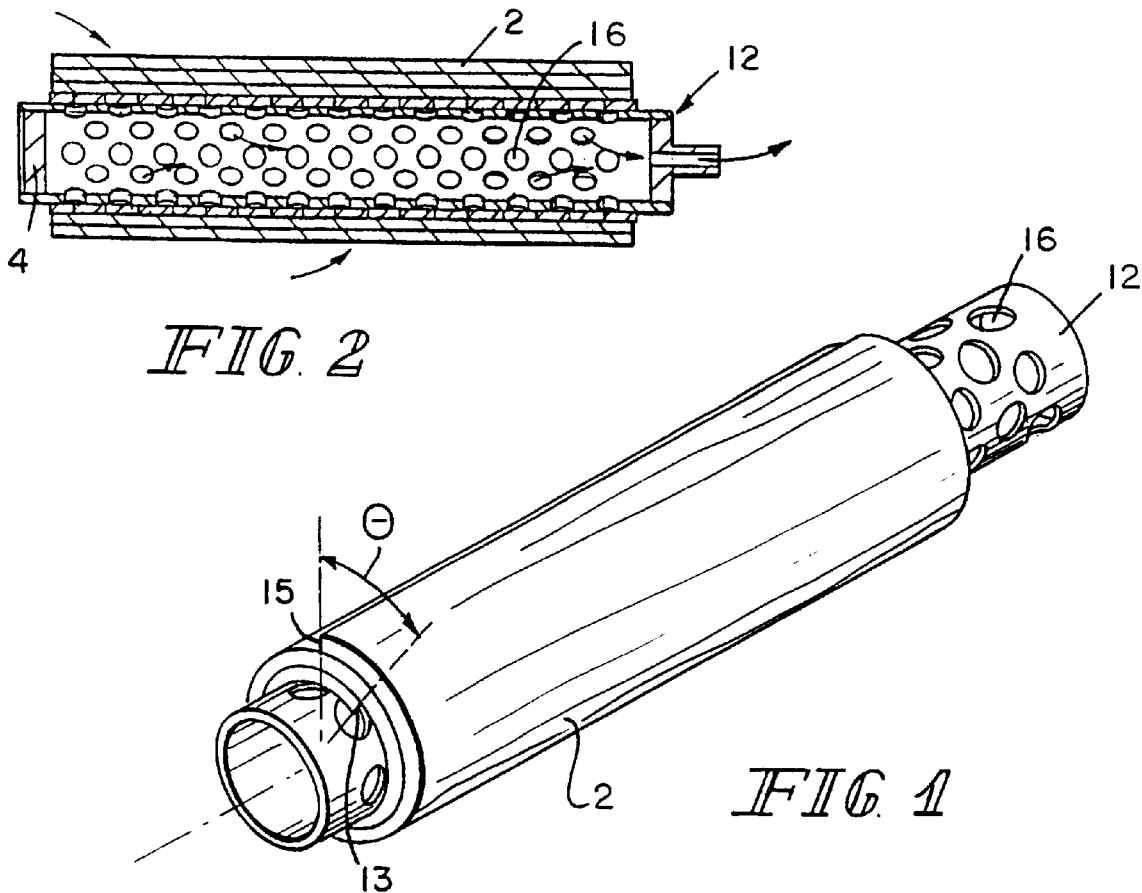
FIG. 2
FIG. 1
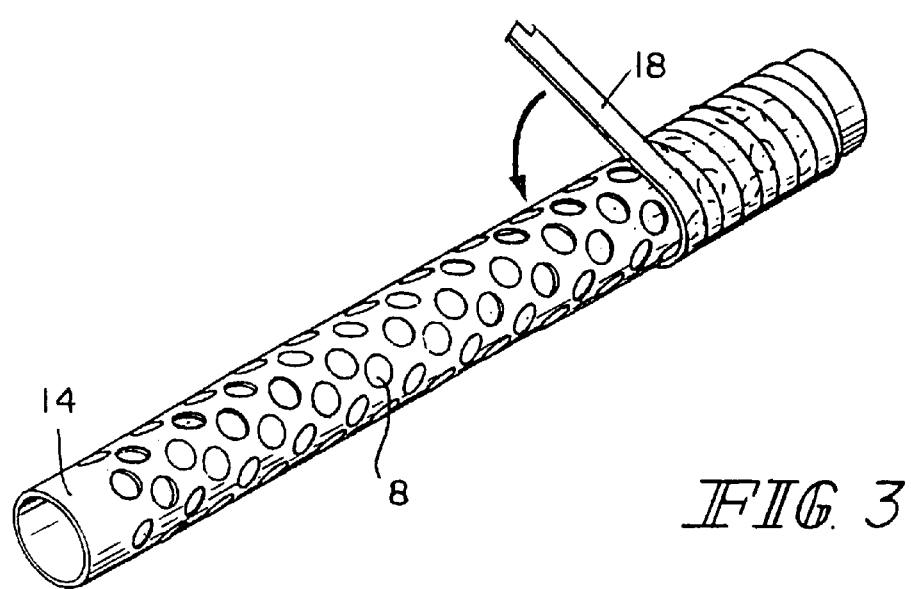
FIG. 3

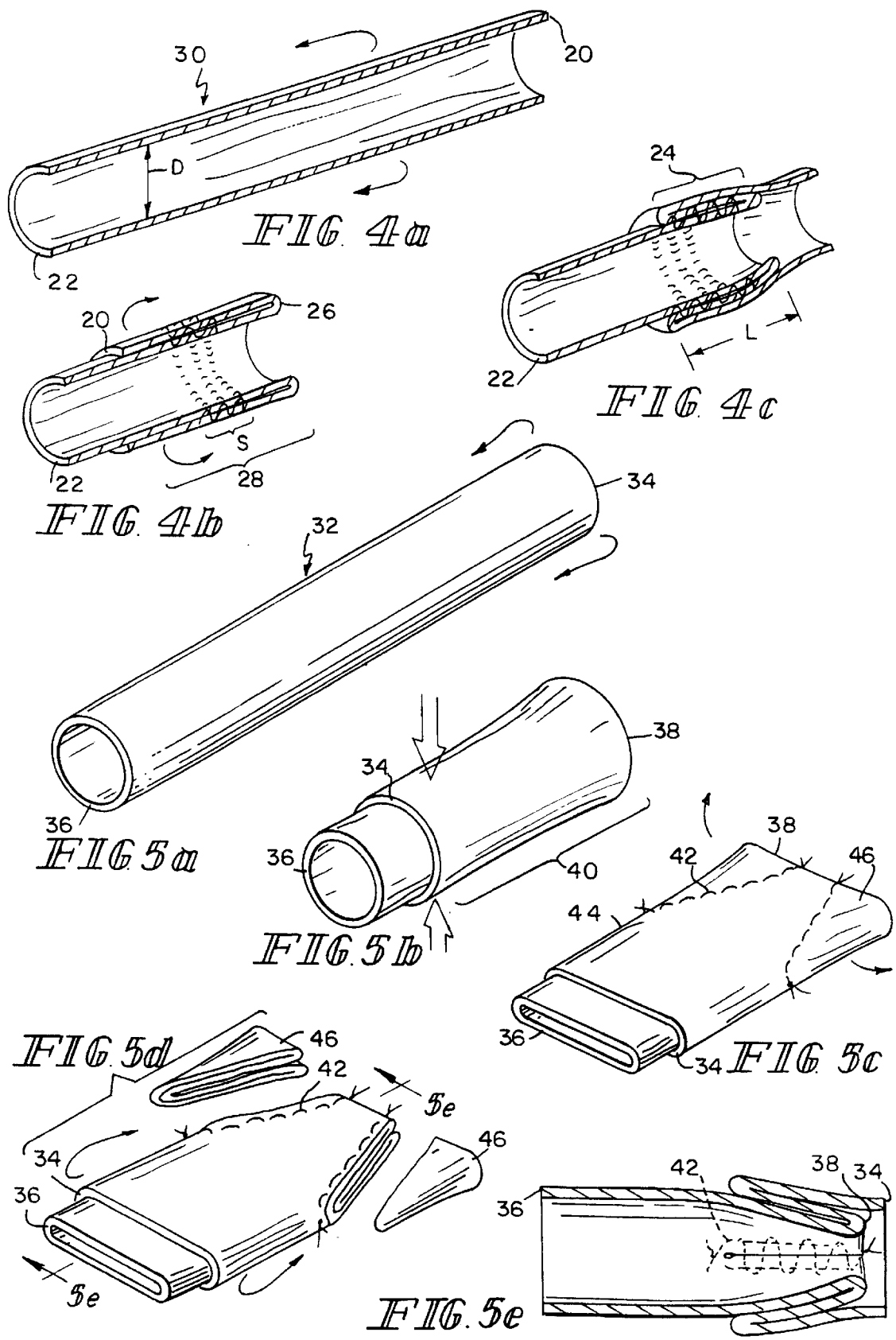

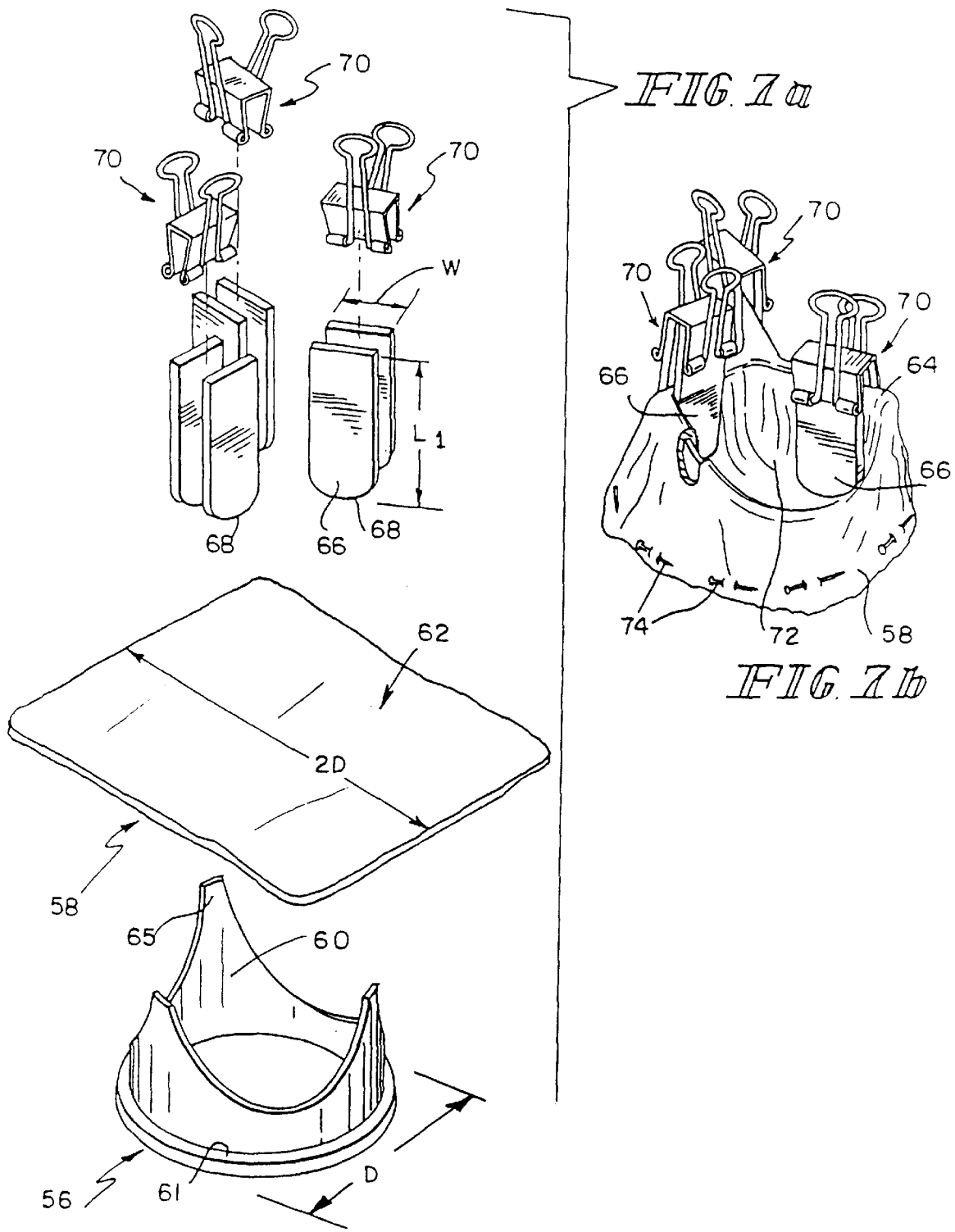

ARTIFICIAL VASCULAR VALVES

CROSS-REFERENCE TO RELATED APPLICATIONS

This application is a U.S. national application of international application serial No. PCT/US97/22728 filed Dec. 10, 1997, which claims priority to U.S. provisional application serial No. 60/032,684 filed Dec. 10, 1996.

FIELD OF THE INVENTION

The present invention relates to a tissue graft composition and method for its preparation and use. More particularly, the present invention is directed to non-immunogenic submucosal tissue graft compositions prepared from warm-blooded vertebrates and formed into vascular valves. The artificial vascular valves of the present invention are useful for replacing damaged or diseased valves of a warm-blooded vertebrate.

BACKGROUND AND SUMMARY OF THE INVENTION

There are four valves in the heart that direct the flow of blood through the two sides of the heart and out to the various organs of the body. The valves located on the left (systemic) side of the heart are: 1) the mitral valve, located between the left atrium and the left ventricle, and 2) the aortic valve, located between the left ventricle and the aorta. These two valves direct oxygenated blood coming from the lungs, through the left side of the heart and into the aorta for distribution to the body. On the right (pulmonary) side of the heart are: 1) the tricuspid valve, located between the right atrium and the right ventricle, and 2) the pulmonary valve, located between the right ventricle and the pulmonary artery. These two valves direct deoxygenated blood coming from the body, through the right side of the heart, into the pulmonary artery for distribution to the lungs, where it again becomes re-oxygenated to begin the circuit anew.

All four of these heart valves are passive structures in that they do not themselves expend any energy and do not perform any active contractile function. They consist of movable "leaflets" that are designed to open and close in response to differential pressures on either side of the valve. The mitral and tricuspid valves are referred to as "atrioventricular valves" because they are located between an atrium and a ventricle of the heart. The mitral valve has two leaflets whereas the tricuspid valve has three leaflets. The aortic and pulmonary valves each have three leaflets, which are more aptly termed "cusps".

Over 150,000 surgical procedures are performed each year to replace diseased cardiac valves worldwide. Two out of three procedures currently employ mechanical valve prostheses. Mechanical valves include caged-ball valves (such as Starr-Edwards valves), bi-leaflet valves (such as St. Jude valves), and titling disk valves (such as Medtronic-Hall or Omniscience valves). Caged ball valves typically comprise a ball made of a silicone rubber located inside a titanium cage, while bi-leaflet and tilting disk valves are made of various combinations of pyrolytic carbon and titanium. All of these valves have a cloth (usually Dacron™) sewing ring so that the valve prosthesis can be sutured to the patient's native tissue to secure the implanted artificial valve.

The main advantage of mechanical valves is their long-term durability. However, currently available mechanical valves suffer from the disadvantage that they are thrombogenic and thus the patient requires lifetime anticoagulant therapy. If blood clots form on the valve, they may preclude the valve from opening or closing correctly or, more importantly, the blood clots may disengage from the valve and embolize to the brain, causing a stroke. Anticoagulant drugs can be administered to reduce the risk of blood clot formation, however such drugs are expensive and potentially dangerous in that they may cause abnormal bleeding which, in itself, can cause a stroke if the bleeding occurs within the brain.

One alternative to mechanical valves are valves constructed from natural tissues. Artificial valves constructed from natural tissues have superior hemodynamic characteristics, and accordingly the clinical use of tissue-based valves is growing faster than the overall valvular prosthesis market. Currently available tissue valves are constructed either by sewing the leaflets of pig aortic valves to a stent (to hold the leaflets in proper position), or by constructing valve leaflets from the pericardial sac (which surrounds the heart) of cows or pigs and sewing them to a stent. The stents may be rigid or slightly flexible and are covered with cloth (usually a synthetic material sold under the trademark Dacron™) and attached to a sewing ring for fixation to the patient's native tissue. Three tissue valves have been approved by the US FDA for implantation: the Carpentier-Edwards Porcine Valve, the Hancock Porcine Valve, and the Carpentier-Edwards Pericardial Valve.

The main advantage of tissue valves is that they do not cause blood clots to form as readily as do the mechanical valves, and therefore, they do not absolutely require systemic anticoagulation. The major disadvantage of tissue valves is that they lack the long-term durability of mechanical valves. Currently available tissue valves have a significant failure rate, usually appearing at approximately 8–10 years following implantation. In particular, currently available tissue valve prothesis calcify after implantation, and calcification of the valves produces stiff leaflets which often crack.

Thus there is a need for a tissue valve construct that has long term durability and is biocompatible with host tissues. The present invention is directed to artificial tissue valves formed from warm-blooded vertebrate submucosal tissue. Submucosal tissue, prepared in accordance with the present invention, has been previously described as a biocompatible, non-thrombogenic graft material that enhances the repair of damaged or diseased host tissues. Numerous studies have shown that warm-blooded vertebrate submucosa is capable of inducing host tissue proliferation, and remodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization are observed and the submucosa material is remodeled into host replacement tissue with site-specific structural and functional properties.

Submucosal tissue can be obtained from various tissue sources, harvested from animals raised for meat production, including, for example, pigs, cattle and sheep or other warm-blooded vertebrates. More particularly, the submucosa is isolated from warm-blooded tissues including the alimentary, respiratory, intestinal, urinary or genital tracts of warm-blooded vertebrates. In general submucosa is prepared from these tissue sources by delaminating the submucosa from both the smooth muscle layers and the mucosal layers. The preparation of intestinal submucosa is described and claimed in U.S. Pat. No. 4,902,508, the disclosure of which is expressly incorporated herein by reference. Urinary bladder submucosa and its preparation is described in U.S. Pat. No. 5,554,389, the disclosure of which is expressly incorporated herein by reference. Stomach submucosa has also been obtained and characterized using similar tissue processing techniques. Such is described in U.S. patent application Ser. No. 60/032,683 entitled STOMACH SUBMUCOSA DERIVED TISSUE GRAFT, filed on Dec. 10, 1996. Briefly, stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica mucosa layers. The resulting stomach submucosa tissue has a thickness of about 100 to about 200 micrometers, and consists primarily (greater than 98%) of acellular, eosinophilic staining (H&E stain) extracellular matrix material.

Preferred submucosal tissues for use in accordance with this invention include intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine.

As a tissue graft, submucosal tissue undergoes remodeling and induces the growth of endogenous tissues upon implantation into a host. It has been used successfully in vascular grafts, urinary bladder and hernia repair, replacement and repair of tendons and ligaments, and dermal grafts. The preparation and use of submucosa as a tissue graft composition is described in U.S. Pat. Nos. 4,902,508; 5,281, 422; 5,275,826; 5,554,389; and other related U.S. patents. When used in such applications, the graft constructs appear not only to serve as a matrix for the regrowth of the tissues replaced by the graft constructs, but also promote or induce such regrowth of endogenous tissue. Common events to this remodeling process include: widespread and very rapid neovascularization, proliferation of granulation mesenchymal cells, biodegradation/resorption of implanted intestinal submucosal tissue material, and lack of immune rejection.

Submucosal tissue is also capable of promoting endogenous regrowth and healing of damaged or diseased cardiac tissues, including the endocardium, pericardium, and myocardium. In particular, damaged or diseased myocardial tissues can be replaced in vivo with a composition comprising submucosal tissue of a warm blooded vertebrate to enhance the formation of endogenous tissues having spontaneous contractile properties.

The present invention is directed to the use of submucosal tissue to prepare tissue valve constructs, and the use of those valve constructs to replace or repair damaged or diseased valves of the heart and the circulatory system of a warm-blooded vertebrate.

BRIEF DESCRIPTION OF THE DRAWINGS

FIG. 1 is a sectional view of a submucosal tissue wrapped mandrel wherein the layers of submucosal tissue are subjected to vacuum pressing.

FIG. 2 is a perspective view of a mandrel wrapped with a sheet of submucosal tissue wherein the two ends of the sheet of submucosal tissue are overlapped to form a tube of submucosal tissue having an overlapped region defined by the overlap angle θ.

FIG. 3 is a perspective view of a mandrel spirally wrapped with a narrow sheet of submucosal tissue to form a tube of submucosal tissue.

FIGS. 4a–4c are sectional views of one embodiment of a vascular valve formed from a tube of submucosal tissue.

FIGS. 5a–5e are perspective views of one embodiment of a vascular valve formed from a tube of submucosal tissue.

FIG. 7a illustrates the components used to form a tricuspid valve.

FIG. 7b illustrates the assembled construct.

FIG. 11a illustrates the operation of the valve in the presence of a forward flow;

FIG. 11b illustrates the operation of the valve in the presence of a reverse flow.

DETAILED DESCRIPTION OF THE INVENTION

Figure 6A:
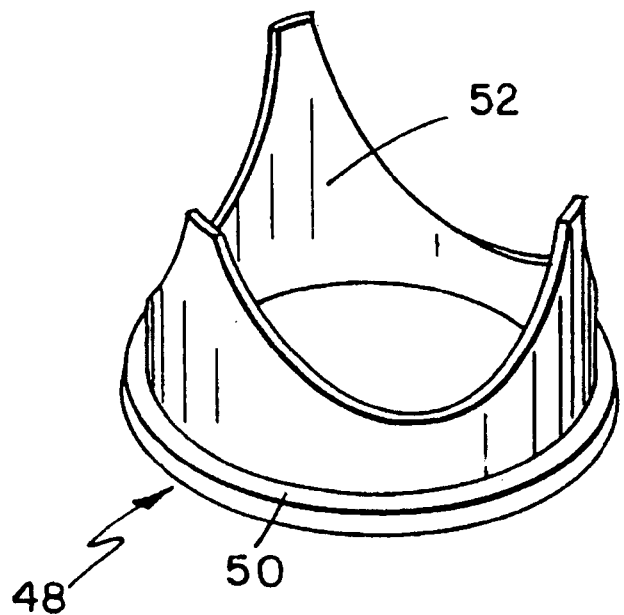
FIG. 6a illustrates a stent having an annular base and three stent post extending from the base.

A variety of tissue sources have been used to fabricate and repair heart valves, including the fascia lata, bovine pericardium and dura mater. In addition, researchers have studied the potential use of animal valves (such as porcine valves) and cadaver valves to replace human valves. Investigators working with tissue valve prostheses have discovered that fresh tissues have a tendency to shrink over time, resulting in the failure of the valves to seal completely and prevent backflow of fluids. Therefore investigators have used glutaraldehyde treatments to stiffen the tissue and prevent subsequent shrinking of those tissues. Advantageously, glutaraldehyde treatment of the tissues also reduces the probability of the tissue implant invoking an immune response. However, the glutaraldehyde treatment also shortens the in vivo lifespan of the tissue valve.

Natural valve leaflets consist of a very pliable spongy material that contains fibrous materials oriented such that the tissue is resistant to stretching but not to compression forces. This low resistance to axial compressive forces give the natural heart valve tissue its characteristic high pliability. When such tissue is fixed with glutaraldehyde, it becomes up to four times stiffer than fresh tissue. The fixation process induces molecular crosslinks resulting in the tissue becoming more resistant to the axial compression forces that accompany bending. As a result the stiffer tissue buckles during bending, and with each successive heartbeat the tissue tends to buckle at the same location, fatiguing the collagen fibers until they break. Furthermore, glutaraldehyde treatment of tissues appears to induce the calcification of the treated tissues (see Example 1). Calcification of the tissues leads to further stiffening of the leaflets aggravating the implant's susceptibility to cracking and failure of the implanted tissue valve.

The present tissue valve prostheses are synthesized from warm-blooded vertebrate submucosal tissue. Submucosal tissue isolated in accordance with the procedures described in U.S. Pat. Nos. 4,902,508 and 5,554,389 does not induce an immune response upon implantation into a host species. Therefore tissue valve constructs prepared from vertebrate submucosal tissue in accordance with the present invention do not need to be treated with glutaraldehyde prior to implantation.

Submucosal tissue can be used to repair an existing valve in vivo by replacing a cusp of a bicuspid or tricuspid valve. Alternatively, submucosal tissue can be used to construct an entire valve to replace a heart valve or other circulatory valve or duct valve. Advantageously, the submucosal tissue of the present valve constructs will induce the formation of endogenous cells and tissues that infiltrate the submucosal tissue and ultimately replace the graft material with endogenous tissue.

The submucosal tissue graft constructs of the present invention can be sterilized using conventional sterilization techniques including glutaraldehyde tanning, formaldehyde tanning at acidic pH, propylene oxide or ethylene oxide treatment, gas plasma sterilization, gamma radiation, electron beam radiation, peracetic acid sterilization. Sterilization techniques which do not adversely affect the mechanical strength, structure, and biotropic properties of the submucosal tissue is preferred. For instance, strong gamma radiation may cause loss of strength in the submucosal tissue. Preferred sterilization techniques include exposing the graft to peracetic acid, 1–4 Mrads gamma irradiation (more preferably 1–2.5 Mrads of gamma irradiation), ethylene oxide treatment or gas plasma sterilization; peracetic acid sterilization is the most preferred sterilization method. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

Submucosal tissue can be stored in a hydrated or dehydrated state. Lyophilized or air dried submucosa tissue can be rehydrated and used in accordance with this invention without significant loss of its biotropic and mechanical properties.

In one embodiment in accordance with the present invention, a single piece vascular valve can be constructed from a tube of warm-blooded vertebrate submucosa. The tubes of submucosal tissue used to form the tissue valves of the present invention are formed to have fluid-tight seams and can be shaped to match the endogenous tissue to be replaced by the graft construct. In one preferred embodiment the vascular valve is formed from a tube of intestinal submucosal tissue and is configured as a duck-bill valve.

Tubes of submucosal tissue can be prepared from a variety of sources including intestinal submucosal tissue delaminated from both the tunica muscularis and at least the lumenal portion of the tunica mucosa as described in U.S. Pat. No. 4,902,508. In brief, a segment of vertebrate intestine, preferably harvested from porcine, ovine or bovine species, but not excluding other species is subjected to abrasion using a longitudinal wiping motion to remove the outer layers, comprising smooth muscle tissues, and the innermost layer, i.e., the luminal portion of the tunica mucosa.

The diameter of the prepared tube of submucosal tissue should be approximately the same as the diameter of the recipient blood vessel. In one embodiment this is accomplished by manipulating the submucosal tissue to define a cylinder having diameter approximately the same as that of the recipient blood vessel and suturing or otherwise securing the submucosal tissue longitudinally to form a tube of the appropriate luminal diameter. Thus, for example, a vascular graft can be prepared by selecting a sterile glass rod having an outer diameter equal to that of the recipient blood vessel, inserting the glass rod into the lumen of the tube of submucosal tissue (for example, submucosal tissue prepared from a segment of intestinal tissue) and gathering the redundant tissue. The desired lumen diameter is achieved by suturing along the length of the graft (for example, using two continuous suture lines or a simple interrupted suture line) or by using other art-recognized tissue securing techniques.

The tube of submucosal tissue can also be formed from a sheet of submucosal tissue. The term "sheet of submucosal tissue" is defined herein to include tissue constructs comprising multiple strips of submucosal tissue, wherein the strips are overlapped and compressed under dehydrating conditions to form a unitary construct having a surface area greater than the surface area of any one of the individual strips used to form said construct. The term sheet of submucosal tissue also includes a tube of intestinal submucosal tissue that is cut along the length of the tube and laid flat.

In one embodiment a tube of submucosal tissue is formed from a sheet of submucosal tissue by wrapping the tissue around a cylindrically shaped mandrel of the appropriate diameter. The excess tissue is removed, and the opposing ends bound to one another to form a tube having a lumenal diameter approximately equal to the diameter of the mandrel. The opposing ends of the sheet can be bound to one another by adhesive pastes, sutures, fusion of the ends by overlapping the tissue and heating under dehydrating conditions or any other fixation technique known to those skilled in the art.

In one embodiment, as shown in FIG. 1, sheets of submucosal tissue 2 are shaped into a tubular structure of any size by spirally wrapping the sheet of submucosal tissue 2 around a cylindrical mandrel 12 of the appropriate diameter and compressing the overlapped tissue under dehydrating conditions. Preferably the mandrel 12 is a hollow cylinder made of plastic or metal having a plurality of holes 16 formed in the cylinder wall. The compression of the tissue can be achieved by forming a seal 4 at one end of the mandrel 12 and pulling a vacuum through the lumen of the mandrel 12 (See FIG. 2). Alternatively, the tissue can be compressed by applying an external force to the exterior surface of the wrapped submucosal tissue to compress the tissue against the mandrel. In one embodiment the final seam of the spirally wrapped tissue can be further secured by sutures, spot-welding with heat or treating the seam with glutaraldehyde.

In accordance with the present invention, the tube of submucosal tissue can be formed as a multilaminate construct wherein one or more sheets of submucosal tissue are wrapped around a mandrel in multiple layers. The dimensions of the individual sheets of submucosal tissue used is not critical and the term "sheet of submucosal tissue" is defined herein to include submucosal tissue from one or more vertebrate sources or organs in a wide variety of sizes and shapes.

In one embodiment the sheet of submucosal tissue 2 has a width equal to the desired length of the formed tube of submucosal tissue, and the tube is formed such that the first edge 13 of the sheet of submucosal tissue 2 is substantially parallel to the second opposite edge 15 of the sheet of submucosal tissue in the formed tube. The second opposite edge 15 extends over the first edge 13 to form an overlapped region defined by the overlap angle θ (See FIG. 1). The sheet submucosal tissue 2 is applied to the mandrel 12 by a rolling motion with the desired number of layers (typically two) and an overlap region (defined by an overlap angle (θ) of about 30 degrees) to form a tube of submucosal tissue having a longitudinally extending seam, as shown in FIG. 1. The wrapped submucosal tissue is compressed against said mandrel under dehydrating conditions for a predetermined time period, and the tubular prosthesis is then removed from the mandrel. The resulting tubular construct has a seam extending the length of the construct. The seam of the tube of submucosal tissue is sealed using techniques known to those skilled in the art including, crosslinking, suturing, binding with adhesives or fusing by compressing under dehdyrating conditions, to resist movement of fluids from the lumen through the seam to the exterior of the tube. This seam can be further secured by spot-welding with heat or with glutaraldehyde.

Alternatively the tube of submucosa can be formed from one or more narrow sheets of submucosal tissue that have a width less than the desired length of the formed tube of submucosal tissue (See FIG. 3). In this embodiment a narrow sheet of submucosal tissue 18 is wound about a mandrel 14 multiple times wherein the narrow sheet is at least partially overlapped leaving no portion of the underlying mandrel exposed. In one embodiment the mandrel 14 is provided with a plurality of holes 8. The amount of overlap in the partially overlapped strips of submucosal tissue ranges between 10–60% of the width of the individual strip and more preferably the overlapped portion is a 50% overlap. In one embodiment multiple sheets of submucosal tissue can be overlaid onto the mandrel, provide that at least a portion of each piece of submucosal tissue overlaps a portion of another piece of submucosal tissue wrapped onto the mandrel.

Submucosal tissue can be conditioned, as described in U.S. Pat. No. 5,275,826 (the disclosure of which is expressly incorporated herein by reference) to alter the visco-elastic properties of the submucosal tissue. In one embodiment the submucosal tissue is conditioned by stretching the graft material longitudinally to a length longer than the length of the submucosal tissue from which the graft construct was formed. One method of conditioning the tissue by stretching involves application of a given load to the submucosa for three to five cycles. Each cycle consists of applying a load to the graft material for five seconds, followed by a ten second relaxation phase. Three to five cycles produce a stretch-conditioned graft material with reduced strain. The graft material does not immediately return to its original size; it remains in a "stretched" dimension. Optionally, the graft material can be preconditioned by stretching in the lateral dimension.

In one embodiment the submucosal tissue is stretched using 50% of the predicted ultimate load. The "ultimate load" is the maximum load that can be applied to the submucosal tissue without resulting in failure of the tissue (i.e., the break point of the tissue). Ultimate load can be predicted for a given strip of submucosal tissue based on the source and thickness of the material. Accordingly, one method of conditioning the tissue by stretching involves application of 50% of the predicted ultimate load to the submucosa for three to ten cycles. Each cycle consists of applying a load to the graft material for five seconds, followed by a ten second relaxation phase. The resulting conditioned submucosal tissue has a strain of less than 30%, more typically a strain from about 20% to about 28%. In one preferred embodiment conditioned the submucosal tissue has a strain of no more than 20%. The term strain as used herein refers to the maximum amount of tissue elongation before failure of the tissue, when the tissue is stretched under an applied load. It is expressed as a percentage of the length of the tissue before loading. The conditioned submucosal strips can be used to form the tubular construct or alternatively the tubular construct can be conditioned after its formation.

In accordance with one embodiment warm-blooded vertebrate submucosa delaminated from the both the tunica muscularis and at least the luminal portion of the tunica mucosa is conditioned to have a strain of no more than 20%. The submucosal tissue is conditioned by stretching, chemically treating, enzymatically treating or exposing the tissue to other environmental factors. In one embodiment the sheets of submucosal tissue are conditioned by stretching in a longitudinal or lateral direction so that the sheets of submucosal tissue have a strain of less than 30%, more typically a strain from about 20% to about 28%. In one preferred embodiment conditioned the submucosal tissue has a strain of no more than 20%.

In addition, a gentle heating treatment can be utilized to stiffen the submucosal tissue and to ensure the shape memory of the tissue. The heat treatment comprises exposing the submucosal tissue to a liquid, preferably water that has been heated to about 65 to about 100° C. The submucosa is exposed to the heated liquid for a brief time period ranging from about 10 seconds to about five minutes. Preferably the entire tissue graft does not equilibrate with the temperature of the liquid medium, but only the surface of the graft reaches the temperature of the medium.

In accordance with one embodiment, a tube of submucosal tissue is utilized to form an artificial vascular valve for replacement of an endogenous defective vascular valve (See FIGS. 4a–4c and FIGS. 5a–5e). In accordance with one embodiment shown in FIGS. 4a–4c the tissue valve construct is in the form of a continuous tube 30 having a diameter (D) approximating the diameter of the defective valve. The continuous tube 30 has a first 20 and second opposite ends 22 and a triple walled intermediate portion 24 having length (L) of about 1.5 D to about 3.5 D. The triple walled portion of the tissue graft is formed by everting the first end 20 of the tube to form a tubular construct having a double walled end 26, and a double walled portion 28 proximal to and extending from said double walled end 26. The two walls of the double-walled intermediate portion are sutured together over a region having a length S, wherein the sutured region is located at least a distance ½ D from the double walled end 26 of the tubular construct. Typically the suture length is about 0.8 to about 5 cm, more preferably about 1 about 2 cm. The first end 20 is reverted over the sutured double-walled portion and the double-walled end 26 of the tubular construct, wherein the ratio of L to S is about 2 to about 5 more preferably about 2.5 to about 3.5. Tissue valves having an overlap/suture ratio (ratio of L to S) in the range of 3.0 to 3.2 provide excellent forward/reverse ratios of approximately 22. These valves also have been shown to work well over a wide range of pressures.

In another embodiment the tissue valve is in the form of a continuous tube having a diameter (D) approximating that of the defective valve. The tube has a first and second opposite ends and a triple walled intermediate portion having length (L) about 1.5 D to about 3.5 D. The triple walled portion of the tissue graft is formed by everting the first end of the tube to form a tubular construct having a double walled end, and a double walled portion proximal to and extending from said double walled end. The first end is then reverted over the double walled portion and the double walled end of the tubular construct, and the three walls of the triple-walled intermediate portion are sutured together to form a sutured portion having a length S of about 0.8 to about 5 cm, more preferably about 1 to about 2 cm. The end of the sutured portion proximal to the double walled end is located at least a distance ½ D from the double walled end of the tubular construct, and the ratio of L to S is about 2.0 to about 5, more preferably about 2.5 to about 3.5.

In another embodiment a single piece artificial valve is constructed from a tube of submucosal tissue 32 having a first end 34 and a second end 36 in accordance with the following method (See FIGS. 5*a*–5*e*). The first end 34 of the tube of submucosal tissue 32 is everted and pulled back over the tube of submucosal tissue 32 to form a double walled end 38 and a double walled portion 40 proximal to and extending from the double walled end 38 (See FIG. 5*b*). The double walled portion 40 is compressed to flatten the tube of submucosal tissue 32 and the tube of submucosal tissue 32 is sealed along two lines extending from the lateral edge 44 of the flattened tube towards one another. In one embodiment a pair of diametrically opposed longitudinal suture lines 42 are used to suture the walls of the double walled portion 40 together. Preferably the pair of suture lines 42 start at the lateral edge 44 of the tube and are angled towards the center of the flatten tube, but the suture lines 42 do not meet (See FIG. 5*c*). After the double walled portion 40 is the tube of submucosal tissue 32 of submucosa has been sutured, the submucosal tissue portions 46 laying outside suture lines 42 are removed (i.e., by cutting). The first end 34 is then reverted over the sutured double-walled portion and the region of the tubular construct where the suture lines 42 meet the lateral edge 44 are sealed, for example by sutures to prevent any leakage of the vessel contents from the lumen to the exterior.

Alternatively a bicuspid or tricuspid valve is constructed using an annular shaped stent in combination with a sheet of submucosal tissue. Typically the stent is constructed from a biocompatible synthetic polymer or from metal that is coated with a biocompatible polymer. However, other material can be used to form the stent, provided that the material has the requisite strength to maintain its shape when inserted into the host. In one embodiment the stent is formed from submucosa that has been treated to stiffen the material. For example the submucosal tissue can be shaped in the form of a stent and then crosslinked, using standard crosslinking agents such as glutaraldehyde and techniques familiar to the skilled practitioner. Alternatively the submucosal tissue can be formed in the shape of a stent and subjected to a heat treatment to stiffen the graft construct. In one embodiment the submucosa based stent is heated in a liquid at a temperature of about 80° to about 100° for about ten seconds to about five minutes.

In one embodiment of the present invention (shown in FIG. 6*a*), a stent 48 comprises a base formed as an annular ring 50 having a plurality of stent posts 52 extending substantially perpendicular to the plane of the annular ring. The stent is selected so that it has a ring diameter approximately the same as the diameter of the vessel that will receive the constructed valve. In one embodiment the external surface of the stent is covered with submucosal tissue so that upon implantation into the host, host tissue will contact only submucosal tissue. Therefore, when the stent comprises a biocompatible synthetic polymer or comprises a biocompatible polymer covered metal, the surface of the stent is optionally first covered with a layer of submucosal tissue before formation of the tissue valve. For example, one or more sheets of submucosal tissue 54 can be wrapped around the stent such that the entire surface of the stent is covered with at least one layer of submucosal tissue (See FIG. 6*b*). After the stent has been wrapped with the submucosal tissue, the tissue can be partially dried to enhance the adherence of the submucosal tissue to the stent. In addition, sutures or other fixation means known to those skilled in the art can be used to secure the submucosal tissue to the surface of the stent.

Alternatively, the stent surface can be covered with submucosal tissue by contacting the stent with fluidized submucosal tissue and then drying the submucosa to form a coating on the stent. For example, a stent coated with fluidized submucosal tissue can be heated to 37° C. for 1–2 hours to dry the fluidized tissue onto the stent. Fluidized submucosal tissue is prepared as described in U.S. Pat. No. 5,275,826, the disclosure of which is expressly incorporated herein.

The bicuspid and tricuspid valves of the present invention can be formed using a single layered sheet of submucosal tissue or a multi-laminate submucosa construct. Multi-laminate submucosal tissue constructs can be formed by overlapping strips of submucosal tissue and binding the overlapped tissues to one another. The overlapped tissues can be bound together through the use of sutures, adhesives, crosslinking agents, heat treatments, or by compressing the tissue under conditions conducive to dehydration of the tissue. Advantageously, large area sheets of submucosa can be formed by partially overlapping strips of submucosa and compressing the tissue under dehydrating conditions to form a unitary heterolaminate graft construct having a surface area larger than any of the strips of submucosa used to form the construct. Alternatively, homolaminate constructs can be prepared by overlaying two or more strips of submucosal tissue and compressing the tissue under conditions conducive to dehydration of the tissue, with or without the use of sutures, adhesives or crosslinking agents.

The submucosal tissue valve prostheses of the present invention have excellent flow dynamics and unlike commercially available glutaraldehyde treated porcine valves, they do not calcify after implantation. Furthermore, the present tissue valve prostheses are optionally heat treated to maintain the proper form of the valve while avoiding/eliminating the disadvantages associated with glutaraldehyde treatments.

The preparation of a multi-cusped vascular tissue valve construct from a sheet of warm-blooded vertebrate submucosa is a multi-step process. First a vascular stent must be selected that has a diameter approximately the same size as the diameter of the vessel that will receive the tissue valve. The stent comprises an annular base and a plurality of stent posts distributed equidistant from one another on the annular base and extending from said base. A stent having two stent posts is used to prepare a bicuspid valve, and a stent having three stent posts is selected for preparation of a tricuspid valve. Each of the stent posts extend from the annular base at the same approximate angle relative to the plane defined by the circumference of the annular base. This angle ranges from about 60° to about 90°, more preferably from about 75° to about 90°. In one embodiment the stent posts extend substantially perpendicularly from the annular base. The multiple stent posts define a luminal space wherein a central axis extends through the center of the annular base and the luminal space equidistant from each of the stent posts.

A single layered sheet or multilaminate sheet is then overlaid onto the stent posts of the stent. Submucosal tissue has an abluminal and a luminal surface. The luminal surface is the submucosal surface facing the lumen of the organ source and typically adjacent to an inner mucosa layer in vivo, whereas the abluminal surface is the submucosal surface facing away from the lumen of the organ source and typically in contact with smooth muscle tissue in vivo. In preferred embodiments the submucosal tissue is overlaid onto the stent with the luminal surface up and the abluminal surface of the submucosa in contact with the surface of the stent. Furthermore, the sheet of submucosa is selected to have a length and width at least twice as large as the diameter of the annular base. In one embodiment the sheet of submucosal tissue is formed as a square piece of tissue having a length and width of 2 D (twice the size of the diameter of the stent annular base). The submucosa tissue is centered over the stent posts and secured to the top of one of the stent posts using standard fixation techniques known to those skilled in the art including clamps, adhesives, sutures or a combination thereof. In one preferred embodiment the submucosa is secured by suturing the tissue to the top of the stent post.

The submucosa tissue is then folded back on itself to form a crease that extends from a point above the top of the submucosa-secured stent post to a point along the central axis of the stent. The tissue is then sequentially secured to the remaining stent posts and the tissue is folded back to form a crease at each remaining stent post in a similar manner as for the first stent post. In accordance with one embodiment, the folded tissue is held in place by compressing the folded tissue between two rigid plates. In one embodiment the crease runs substantially parallel to the line or horizontal plane defined by the top of the stent posts. In an alternative embodiment, the crease is formed at an angle of about 1° to about 45°, more particularly about 1° to about 20° (wherein the origin of the angle is located at the stent post), relative to the line or horizontal plane defined by the top of the stent posts. In accordance with the present invention, the preparation of a bicuspid valve requires the formation of two creases, one running from each of the two stent posts and meeting at a point along the central axis of the stent. The preparation of the tricuspid valve requires the formation of three separate creases, each of which starts at a point above one of the three stent posts and meets at a point along the central axis of the stent. Accordingly the submucosa is sequentially secured to each of the stent posts and the tissue is folded to form a crease that extends from each stent post.

After the appropriate number of creases have been prepared the folded submucosa is optionally subjected to a heat or chemical treatment to stiffen the submucosa and to ensure the shape memory of the tissue. For example, the tissue can be treated with a dilute solution (0.1% to 1%) of a chemical crosslinking agent such as glutaraldehyde to stiffen the tissue. In one preferred embodiment the tissue is stiffened by subjecting the tissue to a heat treatment. The heat treatment in accordance with one embodiment comprises heating the tissue in water at a temperature of about 80° C. to about 100° C. for about ten seconds to about five minutes, more preferably heating the tissue at a temperature of about 88° C. to about 92° C., for about ten to about ninety seconds.

In one embodiment the folded submucosal tissue is clamped between two plates of rigid material, for example metal, plastic, glass or ceramic plates or a combination thereof, and the clamped material is subjected to a heat or chemical treatment to stiffen the submucosa while the tissue remains clamped. The rigid plates are preferably rectangular in shape with a rounded end portion and the plates have a width ranging from about (⅔)D to about(½)D, and a length ranging from about (½)D to about D, wherein D=the diameter of the annular stent base. In one embodiment the plates have a width of about(⅔)D and a length of about ¾ D.

After the submucosa has been clamped and optionally treated, the clamps and plates are removed and the submucosal tissue is secured along the perimeter of the stent posts using standard techniques know to those skilled in the art. In one embodiment the submucosa is secured through the use of sutures. The submucosa is then cut along the creases formed in the submucosa and extending from each of the stent posts to form a commissure. The formed tissue valve is optionally further conditioned by heat or chemically treating the tissue and the heat treatment can be conducted while the tissue valve is subjected to back pressure.

The preparation of a tricuspid valve in accordance with the present invention is described with reference to FIGS. 7a, 7b, 8a and 8b. In accordance with one embodiment of the present invention, a tricuspid valve is formed from intestinal submucosa delaminated from both the tunica muscularis and at least the luminal portion of the tunica mucosa by the following method: An appropriate sized stent 56 having an annular base 61 of diameter D and three stent posts 60 is acquired and is optionally covered with a Dacron mesh or with submucosal tissue as described above. A length of delaminated intestinal submucosal tissue is cut approximately 2 times the outer diameter of the stent. The submucosal tissue segment is then cut longitudinally to form a rectangular submucosa sheet 58 having a length and width of approximately 2 D.

The stent 56 is placed on a horizontal table with its annular base 61 contacting the table. The submucosa sheet 58 is centered over the stent 56 with the luminal side 62 facing up and the submucosal tissue is laid over the stent posts 60 (See FIG. 7a). One of the stent posts is selected for suturing the submucosal tissue to the stent post tip 65. The submucosal tissue is folded at the same stent post where the suture was made and the folded line 64 of submucosal tissue is pulled above the horizontal plane of the stent posts. Two metal plates 66 rectangular in shape (having dimensions W of ⅔ D and $L_1$ of ¾ D) with a curved end portion 68 are used to sandwich the folded submucosal tissue between the plates 66 with the curved end portion 68 of the plate 66 facing down. A flat head paper clip 70 is used to clamp the plates together by fitting it around the stent post 60 (See FIG. 7b).

The commissure position is the only line where a fold should exist (i.e., the submucosal tissue should not be allowed to overlap in areas that is in contact with the plates). Repeat the steps of forming folds of submucosa at each of the remaining stent post locations. The valley of the cusp 72 must have a flat planar appearance (i.e., it should not contain wrinkles).

The excess submucosal tissue is then pinned with pins 74 at the base of the stent 56 between each of the stent posts 60 after the flathead clips 70 are in place. The valve assembly is placed into a pan of near boiling water (approximately 80°–90° C.) and the assembly is removed after about 10 to about 90 seconds. The heat treatment will cause the sheet of submucosal tissue to shrink. The flat head clips 70 and plates 66 are then removed, but the pins 74 at the annular base 61 base are not removed. The submucosa sheet 58 now conforms closely to the top periphery of the stent 56.

Figure 8A:
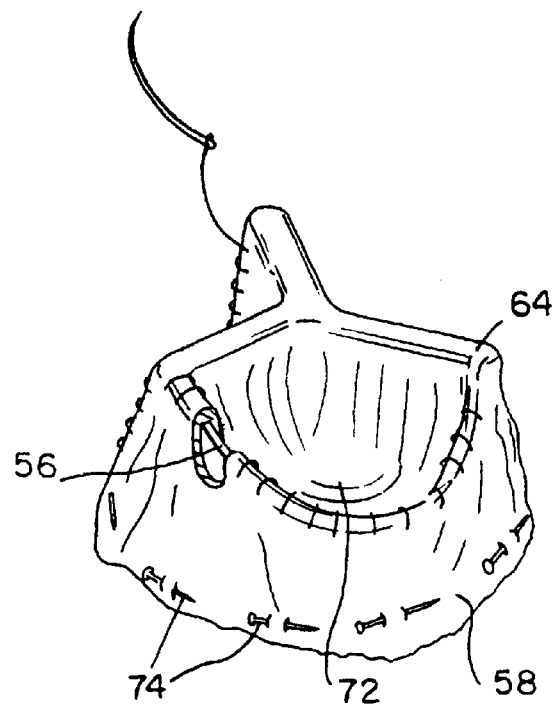
FIG. 8a illustrates a heat treated submucosal tissue covered stent shaped as a tricuspid valve.

The submucosa sheet 58 is then sutured along the periphery of each stent post 60 making certain that the creases that were formed after boiling remain in the same position while suturing (See FIG. 8a). The spacing between the sutures should be less than or equal to 1.5 mm. Pins 74 are then removed from the base of the stent and the excess submucosal tissue around the outside area of the orifice is removed. The assembly is re-clamped between the plates 66 and the flat head clips 70, in the same manner as above and the assembly is placed back into near boiling water (approximately 80°–90° C.) for another 10 to 90 seconds. The assembly is removed from the near boiling water and the clamps and plates are removed.

Figure 8B:
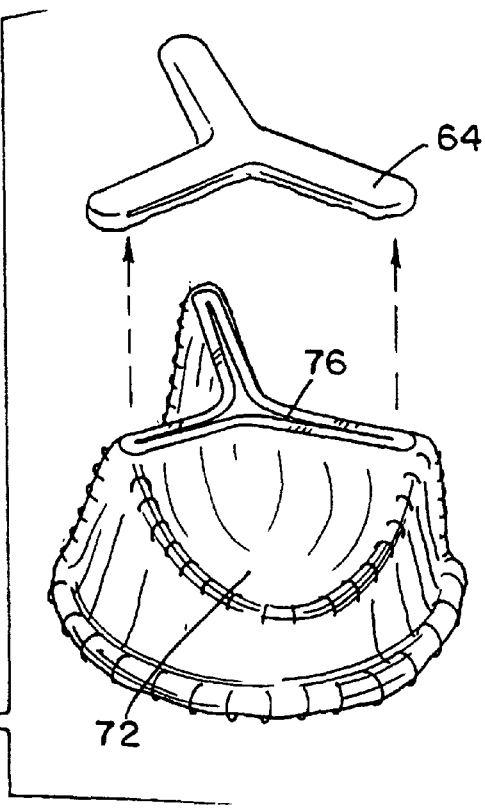
FIG. 8b illustrates the final tricuspid valve tissue graft construct.

The folded submucosal tissue is cut in a horizontal direction from the stent post tip 65 to the center of the luminal space defined by the stent posts 60 to form the commissures (See FIG. 8b). The commissure 76 and the stent post tips 65 should be at approximately the same height and the resultant leaflets must be flush with each other.

The tricuspid synthetic tissue valve prepared in accordance with the method described in the present invention comprises a stent and a layer of submucosa overlaid onto the stent posts. The stent comprises an annular base and three stent posts extending vertically from said annular base, wherein the annular base and the three stent posts define a central axis that extends through the center of the annular base equidistant from each of the stent posts. The submucosal tissue is fixed onto the stent along the perimeter of each of the stent posts, and is folded back upon itself along three radial axes that extend from a point along the central axis to the top of each of the three stent posts. The three folds in the submucosal tissue form the submucosa layer into three concave semi-hemispheres of submucosa. Cutting the folded submucosal tissue along the three radial axes forms the commissures of the heart valve that allow unidirectional flow from the convex side of the valve construct to the concave side. In one embodiment, the commissures of the radial axes of the constructed tissue valve are perpendicular to the central axis and are essentially co-planar with the plane defined by the tips of the stent posts as shown in FIG. 8b.

EXAMPLE 1
Subcutaneous Calcification Studies on Submucosal Tissue

Glutaraldehyde (GA) treatment of biomaterials is known to promote calcification, poor host-tissue incorporation and ultimately mechanical failure of bioprotheses. To anticipate the cardiovascular applications of submucosal tissue, the calcification potential of submucosal tissue and the effect of GA treatment were studied.

Experiment 1

Submucosal tissue treated with peracetic acid (PAA), a mild glutaraldehyde (GA) exposure (0.6% for 5 min.), or rinsed but otherwise untreated, along with cusps from commercial porcine, bioprosthetic heart valves (glutaraldehyde treated by manufacturer) were implanted in the well-established weanling rat model. A specimen 1 cm by 1 cm of each of the 4 tissues was implanted in surgically created subcutaneous pockets on the ventral abdomen of 18 rats. Six rats were sacrificed and tissues harvested and evaluated at 1, 2 and 4 weeks post-implantation. Histologic studies indicated that by 2 weeks all submucosal tissue specimens, except for GA treated specimen, were well incorporated into the surrounding tissue and by 4 weeks all submucosal tissue specimens appeared similar. VonKossa's stain for mineralization indicated that no significant calcification occurred in the PAA or rinsed submucosal tissue specimens at any of the time-periods, but GA treated submucosal tissue and the porcine valve cusps showed significant calcium accumulation-even at the 1-week evaluation period (P=0001).

Experiment 2

Four test samples: 1) native (cleaned, untreated) submucosal tissue, 2) submucosal tissue disinfected with 0.1% peracetic acid (PAA), 3) submucosal tissue treated with 0.25% GA, and 4) commercially available GA-treated porcine bioprosthetic heart valve cusp segments (GPV), were each implanted subcutaneously in each of 24 weanling rats. Six rats were euthanized at 1, 2, 4 and 8 weeks post-implantation for evaluation of calcium concentration by atomic absorption spectroscopy and extent of mineralization and fibrosis by light microscopy.

Materials and Methods

Twenty-four 3-week-old, weanling Sprague-Dawley rats (60–80 g) were allotted to 4 equal groups. One implant (one square centimeter) of each submucosal tissue test material (untreated, PAA-treated and GA-treated) and a segment of commercially available porcine valve cusp was implanted subcutaneously in the abdominal wall of each rat. Calcification of the materials was evaluated histologically and by atomic absorption spectroscopy at 1, 2, 4 and 8 weeks. Extent of calcification and peri-implant fibrosis was graded for comparisons.

Small Intestinal Submucosa

Preparation of submucosal tissue. Harvesting of submucosal tissue has been previously described and will be summarized briefly. A segment of proximal jejunum was obtained from porcine cadavers at an abattoir and prepared as described below within 2 hours of donor pig euthanasia.

All mesenteric tissues were removed from the resected segment of small intestine and the segment was everted. The superficial portions of the tunica mucosa. including the epithelium and lamina propria were removed by gentle abrasion using a longitudinal wiping motion with a scalpel handle and saline-moistened gauze. A moderately dense layer of collagen, specifically identified as the stratum compactum of the basilar tunica mucosa. remained as the surface layer. The segment was then returned to original orientation (inverted) and the tunica serosa and tunica muscularis were removed by similar mechanical abrasion. The remaining thin (0.1 mm thick) whitish, translucent, acellular tube consists of the tunica submucosa with attached stratum compactum and muscularis mucosa of the tunica mucosa. The stratum compactum was the luminal lining.

The submucosal tissue was thoroughly rinsed in sterile water and frozen in liquid nitrogen and stored at −80° C. until use. At the time of sterilization, the submucosal tissue tube was incised longitudinally to make a sheet of submucosal tissue which was cut into 1 $cm^2$ sections and treated by 1 of 3 different protocols.

Native (untreated) submucosal tissue. The 1 $cm^2$ specimens were rinsed 3 times for 15 minutes with sterile water and placed in 5% neomycin sulfate in saline solution and stored at 4° C. until the time of implantation.

Peracetic acid treated submucosal tissue. The 1 $cm^2$ specimens were rinsed with sterile water and treated with 0.1% peracetic acid, then rinsed 3 times for 15 minutes with sterile water. The submucosal tissue was stored in sterile water at 4° C. until the time of implantation.

Glutaraldehyde treated submucosal tissue. The 1 $cm^2$ specimens were rinsed with sterile water and treated with 0.25% glutaraldehyde for 20 minutes, then rinsed 3 times for 15 minutes with sterile water. The submucosal tissue was stored in sterile water at 4° C. until the time of implantation.

Porcine Valve Cusp

The commercially available porcine valve cusp (Hancock porcine valve) was processed according to proprietary methods (Medtronic Inc.). Processing, storage and packaging solution consisted of 0.2% buffered isotonic glutaraldehyde and a bactericidal solution consisting of 1% buffered glutaraldehyde.

One square centimeter sections were cut from the valve cusps. The specimens were rinsed 3 times for 15 minutes in sterile water and stored in sterile water at 40° C. until the time of implantation.

Surgical Procedure and Post-Surgical Care

Anesthesia was induced and maintained with metafane administered via face mask. The ventral abdomen was clipped and prepared for aseptic surgery. One 1.0 cm long longitudinal skin incision was made in each abdominal quadrant and subcutaneous pockets were then created. One 1 cm$^2$ test specimen was randomly placed within each pocket and secured in position with one 5-0 polypropylene suture to the underlying fascia. Skin incisions were closed with a simple interrupted suture pattern with 5-0 polypropylene. One group of animals was euthanized, after anesthesia induction as described above, with intracardiac potassium chloride at 1, 2, 4 and 8 weeks post-implantation. The test materials and associated surrounding tissues were harvested and divided in half. One of these specimens was processed and analyzed by standard histological techniques. The submucosal tissue in the other half of each specimen was isolated and calcium levels determined by atomic absorption spectroscopy.

Mineral Analyses

Samples were immediately frozen in liquid nitrogen and later lyophilized. The dry tissue weight was recorded in milligrams. Mineral analyses of 6N nitric acid in lanthanum chloride (LaCl) of tissue calcium (Ca) was determined by atomic absorption spectroscopy. Elemental concentrations are expressed throughout as micrograms per milligram dry tissue weight (mean±standard error of the mean [SEM]). In addition, pre-implant $Ca^{++}$ analysis was performed on 6 samples of all implant preparations.

Morphologic Analyses

Samples were fixed in Trump's solution for 24 hours, then placed in neutral phosphate buffer. Specimens were embedded in paraffin and sectioned at 6 μm. Sections were stained with hematoxylin and eosin (H&E) for overall morphology and with VorKossa stain to assess mineralization.

Sections were examined by one pathologist by blinded evaluation. Samples were semi-quantitatively scored for peri-implant fibrosis and implant mineralization. Scores were based on a 0(absent), 1(mild), 2(moderate), and 3(severe) grading scale.

Statistical Analyses

Mineralization scores, fibrosis scores and calcium atomic absorption in micrograms per milligram were tested. A General Linear Model Procedure was used to test calcification and fibrosis as functions of post-implantation time and material implanted. A Student Newman Keuls range test was used to detect differences between groups. Significance was determined at p<0.05.

Results

Surgery

No anesthesia deaths were encountered. No wound complications developed and all rats recovered well.

Mineral Analyses

Figure 9:
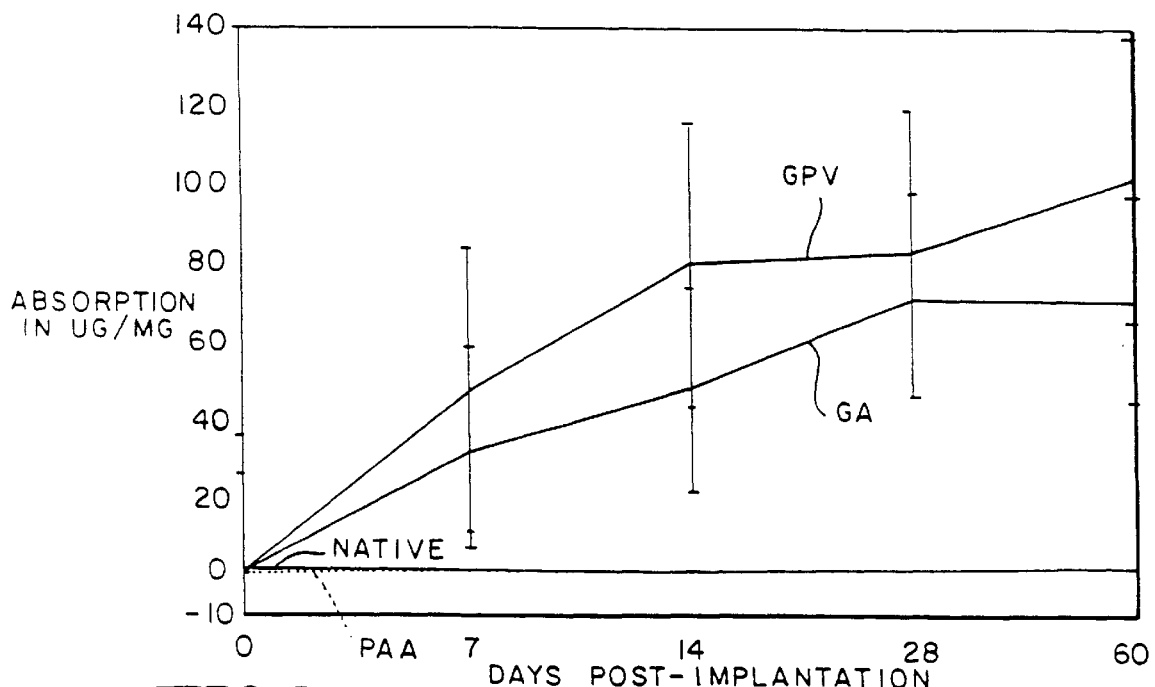
FIG. 9 is a graphic representation of experimental data plotting calcium concentration in implanted native and treated submucosal tissue, as measured by atomic absorption, versus length of implantation time.

The accumulated data measuring the calcium concentration in micrograms per milligram of unimplanted and subcutaneously implanted native, PAA and GA-treated submucosal tissue and GPV are presented in Table 1 an in graphic form in FIG. 9. Tissue samples having a calcium concentration significantly different than that of the other materials are marked in Table 1 with an asterisk (p<0.05, using the Student-Newman-Keuls Test). Calcium content of native and GA-treated submucosal tissue and GPV was not significantly different at Day 0. Notably, PAA-treated submucosal tissue had a significantly lower calcium concentration than the other 3 treatment groups at Day 0. Atomic absorption studies revealed that no calcification occurred in the native or PAA-treated submucosal tissue at any time point when compared with day 0 (pre-implant) calcium concentration. However, statistically significant (p<0.0001) calcification occurred in the GA-created materials (submucosal tissue and GPV) at each implant evaluation time as compared to native and PAA-treated submucosal tissue samples. Histopathologic studies indicated native and PAA-treated submucosal tissue showed no mineralization (p<0.0001) and little peri-implant fibrosis (p<0.0001) and were well-incorporated into surrounding tissue. Calcium concentration was significantly higher in the GA-treated submucosal tissue and the GPV at 1, 2, 4 and 8 weeks post-implantation (Table 1). Time post-implantation and implant material were both statistically significant factors with respect to calcium concentration (p<0.0001).

TABLE 1

Accumulation of calcium in the different groups of tissue after 7, 14, 28 and 60 days of implantation. $\mu gCa^{2+}$/mg dry weight (mean ± s.e.m.)

| Day | 0 | 7 | 14 | 28 | 60 |
|---|---|---|---|---|---|
| Native | 1.53 ± 0.16 | 1.87 ± 0.64 | 0.46 ± 0.11 | 1.33 ± 0.62 | 0.45 ± 0.10 |
| PAA | 0.46 ± 0.24* | 1.20 ± 0.22 | 0.88 ± 0.45 | 0.95 ± 0.23 | 0.47 ± 0.14 |
| GA | 1.00 ± 0.16 | 33.37 ± 4.54* | 48.04 ± 3.49* | 72.23 ± 11.70* | 71.11 ± 11.72* |
| GPV | 1.00 ± 0.09 | 48.25 ± 5.37* | 80.26 ± 4.46* | 83.01 ± 4.95 | 101.38 ± 3.29* |

Morphologic Analyses

At 1 week post-implantation, native and PAA-treated submucosal tissue exhibited a thin zone of surrounding granulation tissue with no mineralization present. The implants showed evidence of incorporation into surrounding tissue by 2 weeks with continued invasion of the implant by Granulation tissue by 4 weeks. At 8 weeks the implant was observed as loose connective tissue with no mineralization or peri-implant fibrosis.

GA-treated submucosal tissue exhibited mild fibrosis surrounding the implant and moderate to marked mineralization by 1 week. By 2 weeks there was moderate invasion of the implant with granulation tissue; however, there was surrounding fibrosis with extensive mineralization of the implant and surrounding connective tissue. By 4 weeks, there was extensive invasion of the implant with granulation tissue and marked mineralization. GA-treated submucosal tissue showed diffuse moderate subacute inflammation and marked multifocal mineralization and mild adjacent fibrosis at 3 weeks.

At 1 week the glutaraldehyde-treated porcine valve (GPV) exhibited a mild to moderate zone of fibrosis surrounding the implant with moderate mineralization. At 2 weeks, there was a fibrous capsule surrounding the implant with occasional associated giant cells. Mineralization was mild to marked. By 4 weeks, the fibrous capsule persisted and mineralization was marked. At 8 weeks, the GPV showed a well demarcated implant with extensive multifocal mineralization, mild surrounding fibrosis, and no indication of surrounding tissue incorporation.

At all time points (1, 2, 4, and 3 weeks post-implantation), mineralization scores were significantly higher in the GA-treated materials (submucosal tissue and GPV) (Table 2). Time post-implantation was not a factor in the mineralization score (p=0.6). Fibrosis scores were significantly higher at weeks 2 and 4 post-implantation in only the GA-created submucosal tissue. However, at week 8 both GA-treated submucosal tissue and GPV had significantly higher fibrosis scores (Table 3). Time was a significant factor in the fibrosis scores (p<0.0001). Implant material was a significant factor in mineralization (p<0.0001) and fibrosis scores (p<0.0001).

TABLE 2

Mean Mineralization Scores

| Day | 7 | 14 | 28 | 60 |
| --- | --- | --- | --- | --- |
| Native | 0 | 0 | 0 | 0 |
| PAA | 0.1 | 0 | 0 | 0 |
| GA | 2.5 | 3 | 2 | 2.5 |
| GPV | 1.7 | 2.4 | 2.7 | 2.4 |

TABLE 3

Mean Fibrosis Scores

| Day | 7 | 14 | 28 | 60 |
| --- | --- | --- | --- | --- |
| Native | 1.3 | 1.3 | 0.8 | 0 |
| PAA | 1.7 | 1.1 | 1 | 0 |
| GA | 1.7 | 2.3 | 2.7 | 0.8 |
| GPV | 1.4 | 1 | 1.3 | 0.8 |

Discussion

The mechanism of calcification secondary to glutaraldehyde fixation of tissue is not well understood. It has been demonstrated that inter- and intramolecular crosslinks occur in native collagen treated with glutaraldehyde and cross-linking appears to be a prerequisite for mineralization of implanted bioprosthetic tissue. The molecular mechanisms by which these reactions permit calcification are not well defined. Specimens of glutaraldehyde-fixed porcine aortic valve mineralize when implanted subcutaneously in rats whereas fresh implants undergo inflammatory organization without mineralization. Calcific deposits in association with connective tissue cells in both porcine aortic valve and bovine pericardium precede those localized to collagen fibrils. This suggests that calcific deposits in bioprosthetic tissue cells and collagen occur by independent mechanisms.

Several studies have investigated various methods to limit calcification of GA-treated bioprostheses. No method has been discovered to totally eliminate calcification. Calcification has been limited by anticalcification agents, new chemical agents based on new methods of cross-linking, improved endothelialization of bioprostheses by means of amino-acids and as a product of intrinsic factors related to composition of the tissue. Apart from these attempts to prevent the process of calcification, no satisfactory solution or biomaterial has yet been formulated.

As noted above, the calcium content, as measured by atomic absorption, of the unimplanted materials was similar in all the tissues before implantation with the exception of PAA-treated submucosal tissue which was significantly lower in calcium content than the other 3 test materials. This may be due to the treatment of the submucosal tissue with peracetic acid and a resultant lowering of the inherent calcium concentration of submucosal tissue.

After implantation native and PAA-treated submucosal tissue had significantly lower calcium concentration at all time points when compared to the GA-treated materials. This was apparent with both the atomic absorption and the histapathologic analyses. Native and PAA-treated submucosal tissue were well incorporated into surrounding tissues by 2 weeks post-implantation. By 8. weeks post-implantation the submucosal tissue was a loose connective tissue with no mineralization or per-implant fibrosis. The GA-treated materials (submucosal tissue and GPV) showed a greater peri-implant fibrotic response. GA-treated submucosal tissue had a slower rate of incorporation into surrounding tissue than the native and PAA-treated submucosal tissue. GA-treated submucosal tissue initially revealed marked peri-implant fibrosis at 1 week post-implantation. At 8 weeks, fibrosis was less. The GPV was not incorporated into surrounding tissues and incited extensive peri-implant fibrosis. At 3 weeks post-implantation, a fibrous capsule persisted and the GPV appeared as a well demarcated subcutaneous implant.

The native and PAA-treated submucosal tissue findings are similar to previous autograft and xenograft studies using submucosal tissue as a vascular graft, and mineralization of the remodeled submucosal tissue/host tissue site has not been found in any previous study. Nor has rejection ever been observed in previous allograft or xenograft studies utilizing intestinal submucosal tissue. Submucosal tissue is essentially an acellular collagen and the collagen molecule is structurally conserved between species.

Results of this study suggest that implants made of native or PAA-treated submucosal tissue have a low potential for calcification in-situ. GA-treated submucosal tissue and a commercial valve cusp developed significant calcification as shown in other biomaterials treated with GA. GA-treated materials show greater inflammatory response, marked mineralization, and a slower rate of incorporation. Native and PAA-treated submucosal tissue incorporated well into surrounding tissues and this is consistent with findings in other studies. For the purpose of comparison, cusps of clinically failed porcine aortic bioprostheses have 202–234 $\mu$g/mg calcium. PAA-treated submucosal tissue at 8 weeks had 0.33–0.61 $\mu$g/mg calcium while GA-treated submucosal tissue had a calcium content of 98–104 $\mu$g/mg at 3 weeks.

The apparent lack of calcification of native and PAA-treated submucosal tissue and the previously demonstrated ability of submucosal tissue to function as a scaffold for host tissue ingrowth and differentiation, makes submucosal tissue the ideal biomaterial for construction of bioprosthetic heart valves and other biodevices. The submucosal tissue is ultimately replaced by endogenous tissues resulting in the formation of a structure that is exclusively host tissue and closely resembles the native structure.

EXAMPLE 2

Single Piece Bicuspid Optimal Design Parameters

Figure 10:
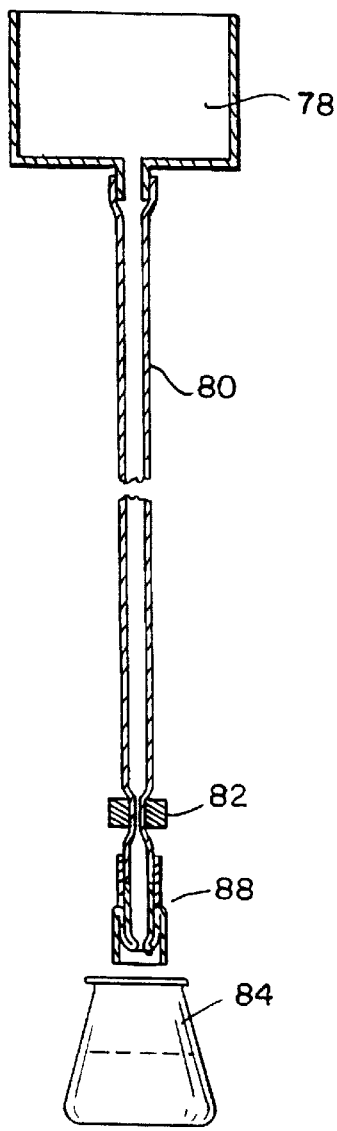
FIG. 10 is a sectional view of testing apparatus for measuring forward and reverse flow rates for tissue valve constructs.

The optimum design parameters for a single piece submucosal tissue valve construct formed from a tube of submucosa was determined by comparative testing of individual forward/reverse flow ratios. The testing apparatus, as shown in FIG. 10, consisted of at large holding tank 78, filled with water, six feet of flexible tubing 80, a tube clamp 82, a large graduated flask 84 and a submucosal tissue valve construct 88.

Figure 11A:
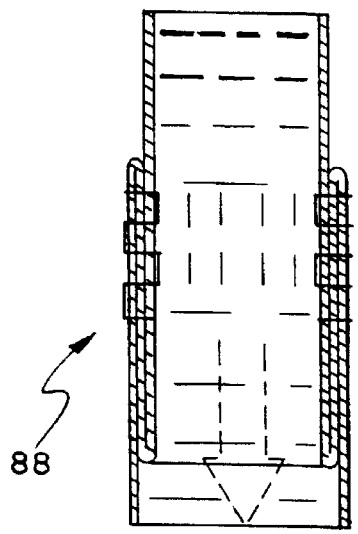
FIGS. 11a and 11b are sectional views of a tissue valve construct formed in accordance with the present invention.
Figure 11B:
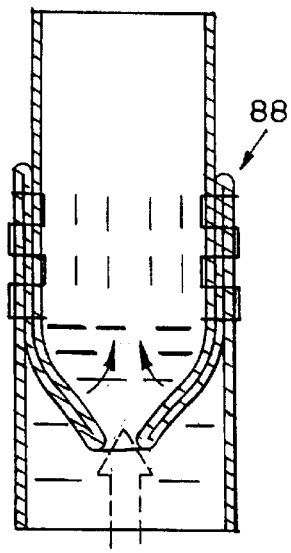

Small intestine submucosa was folded on top of itself and sewn, using #2 suture, in order to attain the bicuspid valve configuration shown in FIG. 11a and FIG. 11b. The submucosal tissue valve construct 88 can be fixed on the end of the flexible tubing 80 in either of two orientations. The first orientation is the forward flow orientation as shown in FIG. 11a that allows fluid to flow through the valve construct. The second orientation, the reverse flow orientation, will prevent the flow of fluids through the valve as shown in FIG. 11b. After the submucosal tissue valve was constructed and attached to the apparatus, water was allowed to flow through the valve in the forward and reverse directions. Water was continually added to the large container so that the pressure could be maintained at a constant valve. The volume of water that flowed through each valve over a certain time period for each given height was recorded. This information could be transformed into comparative data by a few manipulations. The volume flow rate of the water through the valve was determined and plotted versus the given height (h). Each of these graphs was compared via a rough estimate of itsr forward/reverse flow ratios (See Table 4). Although water was the liquid used to measure the pressure in the valve, the information was converted to mmHg so that a standard unit of measurement could be compared.

TABLE 4

| Valve # | Overlap/Suture Length Ratio | Forward/Reverse Flow Ratio |
|---|---|---|
| 1 | 3.5 | 16 |
| 2 | 2.333 | 17.5 |
| 3 | 3.0 | 24.5 |
| 4 | 2.5 | 11 |
| 5 | 2.667 | 6.667 |
| 6 | 2.0 | 12.0 |
| 7 | 2.667 | 11.5 |
| 8 | 2.667 | 10.5 |
| 9 | 3.2 | 23.5 |
| 10 | 3.0 | 21.0 |
| 11 | 1.6 | 12.5 |
| 12 | 1.667 | 2.133 |

|   | Overlap/Length (cm) | Suture Length (cm) |
|---|---|---|
| 1 | 4.445 | 1.27 |
| 2 | 4.445 | 1.91 |
| 3 | 3.87 | 1.27 |
| 4 | 3.175 | 1.27 |
| 5 | 5.08 | 1.91 |
| 6 | 5.08 | 2.54 |
| 7 | 5.08 | 1.91 |
| 8 | 2.54 | 0.953 |
| 9 | 4.763 | 1.588 |
| 10 | 5.715 | 1.91 |
| 11 | 5.08 | 3.175 |
| 12 | 3.175 | 1.91 |

Results & Conclusion

The best forward/reverse flow ratio occurred with valve 3 (See Table 4) with a ratio of 24.5:1. After analyzing the data, the optimum valve design (overlap/suture) ratio appears to be in the 3.0–3.2:1 range. Overlap/suture ratios of this range give very good forward/reverse flow ratios of approximately 22. This range not only gives the optimum forward/reverse flow ratio, but also works very well over a wide range of pressures.

EXAMPLE 3
Tricuspid Valve Construction

Figure 6B:
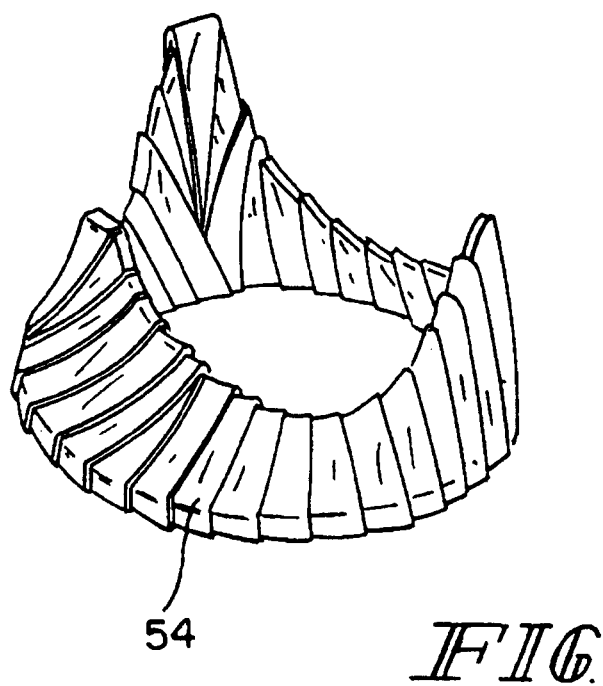
FIG. 6b illustrates the stent of FIG. 6a covered with one or more narrow sheets of submucosal tissue.

The first step in constructing a submucosal tissue valve is to select a stent of the desired diameter (D), as shown in FIG. 6a. The stent is then completely covered by spiral wrapping with a long 1-cm wide strip of dehydrated submucosal tissue, as shown in FIG. 6b. This procedure ensures that only submucosal tissue will contact tissues and blood. A rectangular sheet of submucosal tissue of twice the diameter of the stent is selected and rounded metal cusp-forming plates of thin aluminum with polished edges, and the dimensions shown in FIG. 7a, are used to form the three cusps.

A sheet of submucosal tissue with the luminal side facing up is placed over the stent. One of the stent posts is selected and submucosal tissue is sutured to the post tip. The sheet of submucosal tissue is then folded along a line running perpendicular and extending from the post tip of the stent post where the suture was made. Two of the 6 cusp-forming plates are used to sandwich the folded layers of submucosal tissue between the plates at the same stent post where the suture was made. The curved edges of the plate face downward. The fold of the submucosal tissue is pulled above the horizontal plane of the stent-posts and will form one of the commissure positions of the finished tissue valve. A small binder clip (or other suitable clamp) is then used to clamp the plates together by fitting it around the stent post. The commissure position should be the only line where a fold exists (i.e., no wrinkles are formed in the submucosal tissue in contact with the plates). The procedure is repeated for the remaining two stent-post locations. The valleys of the cusps (i.e., the portion of the submucosal sheet located between the stent posts) must not contain wrinkles. The excess submucosal tissue is pinned to the base of the stent (or fixed to the base by some fixation device known to those skilled in the art) between each of the stent posts after the binder clips are in place (See FIG. 7b).

The submucosal tissue is given a shape memory by heat treatment in water at 90° C. for 15 sec. The sheet of submucosal tissue is then sutured to the periphery of the stent (i.e., along all sides of each stent post and between each stent post), being sure that the creases that were formed after the heat treatment remain in the same position while suturing. The spacing between the sutures should be less or equal to 1.5 mm. The clips and plates are then removed. The pins at the stent base are removed and the excess submucosal tissue around the stent is removed (See FIG. 8a). The folded submucosal tissue is cut carefully with an iris scissor in a horizontal direction from the stent post tip to the center of the orifice to form the commissures. The commissure formation and the tip of the stent post should be at approximately the same height (See FIG. 8b).

A final heat treatment is given by mounting the valve in a fixture and applying hot water at 90° C. with a back pressure of 100 mmHg to provide a uniform coadaptation of the cusps. No sewing ring is needed in this embodiment because the original wrapping of the stent by submucosal tissue provides an adequate structure for suturing. FIG. 8b is an illustration of a submucosal tissue valve made according to the foregoing protocol.

EXAMPLE 4
Tricuspid Valve Testing

Regurgitant flow (leak) and static and dynamic flow tests were performed on the constructed submucosa tissue valves and on the commercially available Hancock porcine and St. Jude Medical mechanical bileaflet valves. More than 50 submucosal tissue valves have been fabricated to date, and leakage and pressure-drop (gradient) studies have been performed on all.

Leakage Tests

Figure 12:
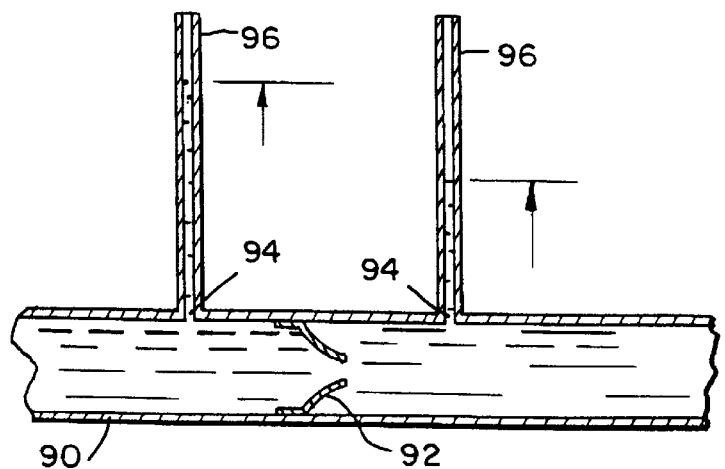
FIG. 12 is a sectional view of a testing apparatus for measuring forward flow resistance and leakage of a constructed tricuspid valve constructs.

FIG. 12 shows the apparatus and method utilized to test the valve constructs for forward flows resistance and leakage. In each test a 100 mmHg static back pressure is applied against the valve under test. The flow rate is measured with a graduated cylinder and stop watch. Because the valves were slightly different in area, the leakage was normalized to the same size (23 mm diameter). Table 5 presents the experimental results for five submucosal tricuspid tissue valves (designated by the Greek letters alpha, beta, delta, kappa and omega) The average regurgitant leakage (48.9 mL/min.) for the five tricuspid tissue valves was slightly less than that for the Hancock porcine valve (62.1 mL/min.) but was much less than that for the St. Jude valve (240 mL/min.).

TABLE 5

| Valve | leakage mL/min |
|---|---|
| alpha | 111.0 |
| beta | 5.0 |
| delta | 58.0 |
| kappa | 54.0 |
| omega | 16.5 |
| Mean Value for submucosal valves | 48.9 |
| Hancock Porcine | 62.1 |
| St. Jude Medical | 240.0 |

For this experiment, no special precautions were taken to align the cusps carefully in these first five tricuspid tissue valves. Those five valve prostheses were prepared with a final heat treatment, but in the absence of heating in the presence of a back pressure as described in Example 3. Heat treating the valves while maintaining a back pressure enhances cusp alignment and reduces regurgitant leakage of the final valve product, considerably.

Forward-Flow Pressure Drop

Figure 13:
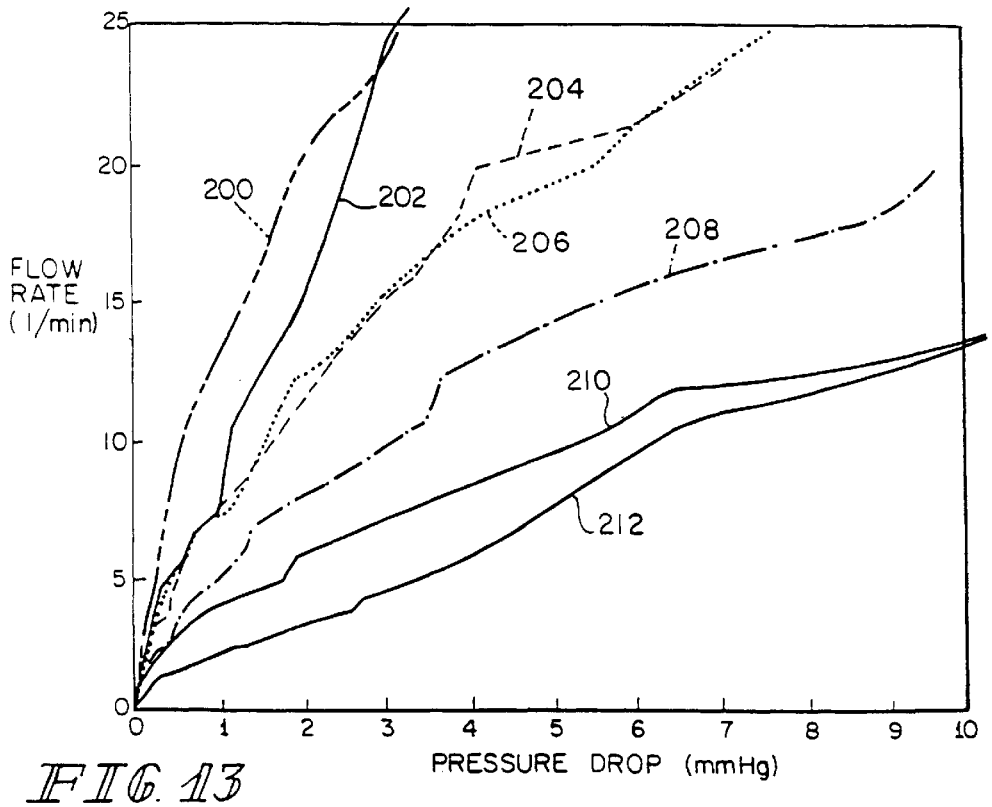
FIG. 13 is a graphic representation of experimental data, plotting flow rate versus pressure drop across various tissue valve constructs.

The resistance to forward flow for the five tricuspid tissue valves, (designated by the Greek letters alpha, beta, delta, kappa and omega), Hancock and St. Jude valves were measured in the manner shown in FIG. 12. The device for measuring resistance to forward flow comprises a central tube 90 having a tricuspid tissue valve 92 fixed within the central tube 90. Ports 94 are formed on either side of the tricuspid tissue valve 92 and are in fluid communication with graduated cylinders 96. Clamp 98 maintains the pressure offset between the two sides of the valve. A pressure of 100 mmHg was used for all measurements. Because the valves were slightly different in area, the flows were normalized to a 23-mm diameter valve. FIG. 13 and Table 6 presents the results. The flow values are mL/min for a 1 mmHg pressure drop across the valve. In other words, the larger the flow (per mmHg), the lower the resistance to flow. The forward-flow rate in liters/min was plotted versus the pressure drop for each of the submucosal tricuspid valves Alpha (208), Beta (204), Delta (206), Kappa (202) and Omega (200) and for the St. Jude (210), and Hancock (212) valves (See FIG. 13). Note that the average flow for the submucosal tissue valves (6.67 L/min. per mmHg) is about five times greater than for the Hancock and St Jude valves. In other words, the average submucosal tissue valve has one fifth the resistance of the Hancock and St. Jude valves.

TABLE 6

Summary of quality tests for submucosal tissue, St. Jude and Hancock heart valves.

| VALVE TYPE | FORWARD FLOW* | BACKWARD FLOW* | QUALITY FACTOR** |
|---|---|---|---|
| Hancock | 1.25 | $0.62 \times 10^{-3}$ | 2,016 |
| St. Jude | 1.25 | $6.67 \times 10^{-3}$ | 187 |
| submucosal tissue Average | 6.67 | $0.48 \times 10^{-3}$ | 13,895 |

*Flow = Liters/min per mmHg.
**Quality Factor = Forward Flow/Backward Flow

Quality Factor

The quality factor of a valve is defined as the ratio of forward flow to backward flow in mL/min per mmHg. Because the quality factor is the ratio for the forward-flow slope to the backward-flow slope, it is clear that the quality factor for an ideal valve would be infinity. The quality factors for the submucosal tissue, Hancock and St. Jude valves were calculated and appear in Table 6. The average quality factor for the submucosal tissue valves was 13,895, whereas that for the Hancock valve was 2016 and the value for the St. Jude was 187. The high quality factor for the submucosal tissue valve is due to its low forward pressure drop and low leakage.

Dynamic tests

The St. Jude, Hancock and submucosal tissue valves were placed in a hydraulic cardiovascular simulator to simulate the environmental conditions between the left ventricle and aorta and demonstrate dynamic valve motion. The mechanics of the St. Jude, Hancock and a typical submucosal tissue valve (Kappa) were measured and compared. In all three cases the valves demonstrated rapid valve closure, with slightly more ringing with the submucosal tissue valve, probably because of the very low mass of its cusps.

The pressure drop across the submucosal tissue valves in forward flow is much less than the two commercially available valves tested, the Hancock porcine aortic valve xenograft and the St. Jude Medical bileaflet mechanical valve. Leakage of the submucosal tissue valve under a backward pressure is almost as small as the Hancock valve, which leaks less than one percent of the typical forward flow, and several times better than the St. Jude valve. Furthermore the synthetic valves of the present invention have been tested and perform well in a hydraulic model of the cardiovascular system.

EXAMPLE 5

Implantation of Submucosal Tissue Heart Valves

Previous studies have indicated that implantation of an artificial valve in sheep for 2 months is equivalent to 10 years in a human in terms of biological processes such as healing and calcification. Therefore sheep were selected for these experiments. Hand-made, pretested submucosal tissue valves are implanted in the mitral location of 50 juvenile sheep. Each valve is screened by bench-top testing for quality and proper flow characteristics and sterilized with peracetic acid prior to implantation. The sheep are divided into four groups with survival times of 1, 3, 6 or 12 months. Twenty-five sheep are studied each year, and each animal is closely monitored for signs of valve malfunction, failure, or infection. In vivo contrast and ultrasound studies are performed to evaluate the valve function prior to explanation. The explanted valves, bench-tested for flow characteristics or subjected to microscopic and chemical analysis. Approximately one third of the explanted valves from a given survival period are reserved for the ex-vivo, bench-top flow studies, while the remaining explants are reserved for the tissue-characterization studies. Bench-tests make comparisons to the pre-implantation (and pre-remodeling) flow-studies possible. Light microscopy is used to characterize the host response to the implant and the extent of tissue remodeling, while electron microscopy is used to evaluate changes in tissue structure (transmission) and extent of endothelialization (scanning). Atomic absorption techniques are employed for quantitation of calcium in the explanted valves.

Submucosal Tissue Preparation

Sections of porcine small intestine are harvested following euthanasia of the animal and placed in chilled, 0.9% saline solution immediately. Sections are cut into the desired lengths, and all mesenteric tissues are removed. The intestine is first everted and the tunica mucosa is abraded using a longitudinal wiping motion with a scalpel handle and moistened gauze. The specimen is then everted to its original orientation. The serosa and tunica muscularis are gently removed from the other surface of the intestinal tube using the same abrasion technique as described for the mucosal surface. The remaining thin (0.1 mm wall thickness), whitish, translucent tube consists of the stratum compactum and muscularis mucosa of the tunica mucosa and the attached submucosa. This tube of acellular collagen-based material is about 40 mm in diameter when removed from a 300-pound sow. Following preparation, the submucosal tissue is rinsed with saline and stored in a 10% neomycin sulfate solution in the refrigerator. Finally, the submucosal tissue is treated with a 0.1% peracetic acid solution for disinfection, rinsed in sterile water and stored in sterile water at approximately 4° C.

Submucosal Tissue Valve Selection

The submucosal tissue valves for implantation are constructed as described in Example 3. The submucosal tissue is screened for obvious imperfections, and the completed valves are bench-tested to determine forward flow resistance, regurgitant flow characteristics, and quality factor. Only those valves with a quality factor greater than 10,000 are implanted.

Surgical Procedure

Juvenile sheep, less than 6 months of age, are the recipients of the new submucosal tissue valves. These valves are implanted into the mitral location of the sheep heart using an aseptic surgical procedure. Anesthesia is induced by injection of sodium thiopental (10 mg/kg i.v.), and a surgical plane of anesthesia is maintained by inhaled isoflurane. A right thoracotomy at the 4th intercostal space is performed and cardiopulmonary bypass is established. The native mitral valve is then removed, and a 23-mm submucosal tissue valve is implanted in the mitral position. Normal cardiopulmonary circulation is then restored and the thorax closed. Chest drainage is maintained until the animal has completely recovered from anesthesia.

Short-term anticoagulation is used in these animals. Immediately prior to establishment of cardiac bypass 250 units/kg of heparin is given intravenously, and immediately following cessation of bypass the heparin is reversed with i.v. prolamine. For three post-operative days, the sheep receive 1000 units of heparin, twice daily, by subcutaneous injection. After this period, all anticoagulation treatments cease.

Post-Operative Care and Valve Harvesting

Each animal is monitored during the recovery and survival periods. Food and water intake and output, temperature, blood chemistry, hemolysis and cell counts are observed at regular intervals for each animal. In addition, ultrasonic imaging on the awake sheep is used to visualize the valve function during the growth period. Clinical signs of infection or cardiac decompensation secondary to valve failure (such as obvious hanging of the head or symptoms of pneumonia) are cause for euthanasia. Infected valves are not included in calcium quantitation due to the likelihood of calcified vegetations.

At the end of the designated survival period, each animal undergoes a terminal study protocol including left heart catheterization, pressure-flow studies, radiographic contrast evaluation, and ultrasonic imaging. Finally, the animal is given a lethal dose of intravenous barbiturate.

A full postmortem evaluation is performed and the valve is harvested and examined for incorporation of the stent into the surrounding issue and pannus encroachment on the valve leaflets. The inflow and outflow aspects of the valve are inspected for mature, "white" clot and fresh, "red" clot formation.

The submucosal tissue valve undergoes the post-harvest, ex-vivo flow studies within 6 hours of euthanasia or the valve is divided into thirds. One of these sections is fixed in zinc-formalin for light-microscopy; one is placed in universal fixative for electron microscopy; and the third is preserved for quantitative calcium determination by atomic absorption and VonKossa's method.

Valvular Flow Studies

The flow characteristics of the submucosal tissue valve are measured before, during and after implantation, and these studies are divided into two groups-in-vivo and ex-vivo testing.

In-Vivo Measurements

Ultrasonic imaging is performed on the awake animals prior to surgery and at selected intervals thereafter. A terminal ultrasound along with right-heart catheterization for contrast angiography, pressure studies and thermal dilution cardiac output determinations are performed on anesthetized animals prior to euthanasia.

Ex-Vivo Measurements

The ex-vivo flow studies are performed on newly-made and newly-explanted submucosal tissue valves using an MP3 pulse-duplicator (Dynatek Laboratories, Galena, Mo.). The parameters measured for each valve include forward flow resistance at several flow rates, effective orifice area, closing volume, regurgitant volume, and overall quality factor.

The initial tests provide baseline values for the performance characteristics of the implanted valves as well as a method for screening the best valves for implantation. The follow-up tests provide results for comparisons with pre-implantation values and for correlation with any clinical observations during the implantation period.

Explant Characterization

Histopathology

A combination of standard stains and immunohistochemical techniques are used to evaluate the valve explants. Hematoxylin & Eosin staining is used to evaluate remodeling of the submucosal tissue and incorporation into the host tissue. VonKossa's stain for calcium deposition is used to visually evaluate valve mineralization, and trichrome-stained sections (e.g., Van Gieson's) are examined for cellularity, microstructure and morphology. Factor VIII related antigen staining (Dako Corp. Carpinteria, Calif.) is used to determine the presence of endothelial cells in the sections, and another antibody (10C2) is applied to evaluate the resorption process of the submucosal tissue valve grafts. All immunohistochemical procedures use the avidin-biotin complex (ABC) method described by Hsu et al. (1981).

Chemical Analysis

Atomic absorption spectroscopy and VonKossa's histological methods are used to quantitate the mineralization of the submucosal tissue valves. Calcium deposited in the valve during the implantation period is measured from within one third of each explant. This value is determined in micrograms of calcium per milligram of tissue by atomic absorption or in terms of a semi-quantitative, mineralization score from the histological sections, and these data are useful for comparison to the results for other tissue valves.

Electron Microscopy

Approximately one third of each explanted submucosal tissue valve is submitted for electronmicroscopic (EM) evaluation. Of particular importance is the structure and fiber orientations found it the leaflet tissue and the extent of endothelialization on the leaflets. Transmission EM is used for the structural views, and scanning EM is used for the surface views. Sections from unimplanted, submucosal tissue valves are studied for comparison to the remodeled tissue of the valve explants.

What is claimed is:

1. A tissue graft in the form of a bicuspid valve for replacement of a defective vascular valve, said tissue graft comprising submucosal tissue, delaminated from both the tunica muscularis and at least the lumenal portion of the tunica mucosa, in the form of a continuous tube having a diameter (D) approximating that of the defective valve said tube having first and second opposite ends and a triple walled intermediate portion having length (L) about 1.5 D to about 3.5 D;

said triple walled portion of the tissue graft being formed by everting the first end of the tube to form a tubular construct having a double walled end and a double walled portion proximal to and extending from said double walled end and reverting said first end over the double walled portion and the double walled end of the tubular construct;

wherein the two walls of the double-walled portion are sutured together to form a sutured portion having a length S and the end of the sutured portion proximal to the double walled end is located at least a distance ½ D from the double walled end, and the ratio of L to S is about 2.5 to about 3.5.

2. The tissue graft of claim 1 wherein the three walls of the triple-walled portion are sutured together to form a sutured portion having a length S and the end of the sutured portion proximal to the double walled end is located at least a distance ½ D from the double walled end, and the ratio of L to S is about 2.5 to about 3.5.

3. The graft construct of claim 1 wherein the two walls of the double-walled portion are sutured together using diametrically opposed longitudinal sutures, and sections of the double walled portion located proximal to and extending from the diametrically opposed sutures are removed from the graft construct before reverting said first end over the double-walled portion.

4. A method of forming a synthetic tissue valve, said method comprising overlaying a sheet of submucosal tissue onto a stent having a plurality of stent posts an annular base, and a central axis, wherein the submucosal tissue contacts the posts of the stent;

fixing the submucosal tissue to the tips of the stent posts;

folding the sheet of submucosal tissue to form folds that extend from the top of each stent post to a point along the central axis;

conditioning the tissue to retain the shape of the tissue;

fixing the submucosal tissue to the sides of the stent posts and the base of the stent; and cutting the fold in the submucosal tissue to form the commissures of the valve.

5. The method of claim 4 wherein the tissue is conditioned by heat treatment.

6. The method of claim 5 wherein the step of folding the submucosa comprises folding the submucosa along an axis extending from the tip of the submucosa-secured stent post to a point along the central axis, and clamping the two layers of each fold of submucosa together before the heat treatment.

7. The method of claim 5 further comprising the step of subjecting the vascular valve to second beat treatment after formation of the commissures.

8. The method of claim 7 wherein the valve is subjected to back pressure during the second heat treatment.

9. The method of claim 5, wherein the sheet of submucosal tissue has a luminal surface and an abluminal surface and is overlaid onto the stent posts with the luminal surface in contact with the stent.

10. The method of claim 5, wherein the stent is provided with three stent posts and the tissue valve is formed as a tricuspid valve.

11. The method of claim 5, wherein the stent is provided with two stent posts and the tissue valve is formed as a bicuspid valve.

12. The method of claim 6 wherein the folded submucosa layers are clamped between two rigid plates.

13. The method of claim 12 wherein the annular base has a diameter of D, and the rigid plates have a length of about ¾ D and a width of about ⅖ D.

14. A synthetic tissue valve comprising a stent, comprising an annular base and three stent posts that extend vertically from said annular base, wherein the annular base and the three stent posts define a central axis that extends through the center of the annular base equidistant from each of the stent posts; and a layer of submucosa overlaid onto the stent posts and fixed onto the stent along the perimeter of each of the stent posts, said submucosa being folded back upon itself along three radial axes that extend from a point along the central axis to the top of each of the three stent posts to form the submucosa layer into three concave semi-hemispheres of submucosa, said submucosa having a slit cut along the folds formed at the three radial axes to allow unidirectional flow from the convex side of the submucosal tissue to the concave side.

15. The synthetic tissue valve of claim 14 wherein the concave side of the submucosal tissue is the luminal side of the submucosal tissue.

16. The synthetic tissue valve of claim 14 wherein each of the radial axes are perpendicular to the central axis.

17. The synthetic tissue valve of claim 14, wherein the stent posts project from the annular ring substantially parallel to the central axis.

18. The synthetic tissue valve of claim 14, wherein the entire surface of the stent is covered with submucosal tissue.

* * * * *